United States Patent
Iversen et al.

(10) Patent No.: US 7,402,574 B2
(45) Date of Patent: Jul. 22, 2008

(54) ANTISENSE COMPOSITION AND METHOD FOR TREATING CANCER

(75) Inventors: Patrick L. Iversen, Corvallis, OR (US); Hemant K. Roy, Highland Park, IL (US); Richard K. Bestwick, Corvallis, OR (US)

(73) Assignee: AVI BioPharma, Inc., Corvallis, OR (US)

( * ) Notice: Subject to any disclaimer, the term of this patent is extended or adjusted under 35 U.S.C. 154(b) by 278 days.

(21) Appl. No.: 11/077,871

(22) Filed: Mar. 10, 2005

(65) Prior Publication Data

US 2005/0261249 A1    Nov. 24, 2005

Related U.S. Application Data

(60) Provisional application No. 60/552,835, filed on Mar. 12, 2004.

(51) Int. Cl.
*A61K 31/70* (2006.01)
*C07H 21/04* (2006.01)

(52) U.S. Cl. ........................................ 514/44; 536/24.5

(58) Field of Classification Search ........................ None
See application file for complete search history.

(56) References Cited

U.S. PATENT DOCUMENTS

| | | | |
|---|---|---|---|
| 5,185,444 | A | 2/1993 | Summerton |
| 6,060,456 | A | 5/2000 | Arnold et al. |
| 6,133,246 | A | 10/2000 | McKay et al. |
| 6,228,579 | B1 | 5/2001 | Zyskind et al. |
| 6,239,265 | B1 | 5/2001 | Cook |
| 6,495,663 | B1 | 12/2002 | Rothbard et al. |
| 6,677,153 | B2 | 1/2004 | Iversen |
| 6,784,291 | B2 | 8/2004 | Iversen et al. |
| 6,828,105 | B2 | 12/2004 | Stein et al. |
| 6,841,542 | B2 | 1/2005 | Bartelmez |
| 7,049,431 | B2 | 5/2006 | Iversen et al. |
| 7,094,765 | B1 | 8/2006 | Iversen et al. |
| 2003/0171335 | A1 | 9/2003 | Stein et al. |
| 2004/0006030 | A1 | 1/2004 | Monia et al. |

OTHER PUBLICATIONS

Agrawal et al.,"Site-specific excision from RNA by RNase H and mixed-phosphate-backbone oligodeoxynucleotides." *Proc Natl Acad Sci U S A*, 87(4):1401-5 (1990).
Barker et al., *Trends Mol. Med.*, 7(12):535-537 (2001).
Batlle,*Nat Cell. Biol.*, 2(2):84-89. (1998).
Bennett, M.R. and Schwartz, S.M., *Circulation*, 92(7):1981-1993 (1995).
Birchmeier and Behrens, *Biochim Biophys ACTA*, 1198(1):11-26.
Blanco et al., Oncongene, 21(20):3241-3246 (2002).
Bloomers et al., *Nucleic Acids Research*, 22(20):4187-4194 (1994).
Bonham et al., "An assessment of the antisense properties of RNase H-competent and steric-blocking oligomers." *Nucleic Acids Res* 23(7):1197-203 (1995).
Boudvillain et al., "Transplatin-modified oligo(2'-O-methyl ribonucleotide)s: a new tool for selective modulation of gene expression." *Biochemistry*, 36(10): 2925-31 (1997).
Bussemakers et al., *Biochem. Biophys. Res. Commun.*, 203(2):1284-1290 (1994).
Cano et al., *Nat. Cell. Biol3.*, 2(2):76-83 (2000).
Carver et al., *Mol. Cell. Biol*, 21(23):8184-8188 (1994).
Cavallaro et al., *Cancer Letters*, 176(2):123-128 (2002).
Corpet et al., *Cancer Epidemiol. Biomarkers Prev*, 12(5):391-400 (2003).
Dagle et al., "Targeted elimination of zygotic messages in *Xenopus laevis* embryos by modified oligonucleotides possessing terminal cationic linkages", *Nucleic Acids Res.*, 28(10):2153-7 (2000).
Ding, D., et al., *Nucleic Acids Res.*, 24(2):354-60 (1996).
Fearon et al., *Cancer Cell.*, 3(4):307-310 (2003).
Felgner et al., *PNAS*, 84(21): 7413-7 (1987).
Gait et al., *J. Chem. Soc.*, 0(14):1684-1686 (1974).
Gee, J. E., et al., *Antisense Nucleic Acid Drug Dev.*, 8(2):103-11 (1998).
Giroldi et al., *Biochem. Biophys. Res. Commun.*, 241(2):453-458 (1997).
Grille et al., *Cancer Res.*, 63(9):2172-2178 (2003).
Hajra et al., *Cancer Res.*, 62(6):1613-1618 (2002).
Hemavathy et al., *Gene*, 257(1):1-12 (2000).
Hirohashi S., *Am. J. Pathology*, 153(2):333-339 (1998).
Hudziak et al., *Antisnese &Nucleic Acid Drug Dev.*, 10(3):163-176 (2000).
Jiao et al., *Br. J. Cancer*, 86(1):98-101 (2002).
Kinzler et al., *Cell*, 87(2):159-170 (1996).
Kishimoto et al., *Gut*, 47(6):812-819 (2000).
Lappalainen et al.,*Biochim Biophys ACTA*, 1196(2):201-208 (1994).
Lesnikowski et al., "Octa(thymidine methanephosphonates) of partially defined stereochemistry: synthesis and effect of chirality at phosphorus on binding to pentadecadeoxyriboadenylic acid." *Nucleic Acids Res.*, 18(8): 2109-15 (1990).
Llorens et al., *Lab Invest.*, 78(9):1131-1142 (1998).
Lou et al., *J. Biomaterials Appl.*, 15(4):307-320 (2001).
Mertes, M. P. and E. A. Coats (1969). "Synthesis of carbonate analogs of dinucleosides. 3'-Thymidinyl 5'-thymidinyl carbonate, 3'-thymidinyl carbonate." *J Med Chem.*, 12(1): 154-7.
Moser et al., *Science*, 247(4940):322-324 (1990).

(Continued)

*Primary Examiner*—Tracy Vivlemore
(74) *Attorney, Agent, or Firm*—King & Spalding LLP

(57) ABSTRACT

A method and composition for treating colorectal cancer is disclosed. The method involves administering to a subject, a therapeutically effective amount of a morpholino antisense compound (i) having a nuclease-resistant backbone, (ii) capable of uptake by target cancer cells in the subject, (iii) containing between 10-40 nucleotide bases, and (iv) having a base sequence effective to hybridize to a region of processed or preprocessed human SNAIL RNA transcript.

12 Claims, 3 Drawing Sheets

OTHER PUBLICATIONS

Nieto et al., *Nat. Rev. Mol. Cell Biol.*, 3(3):155-166 (2002).
Nyormoi, O. and Bar-Eli, M., *Clin Exp Metastasis*, 20(3):251-63 (2003).
Perez-Losada et al., *Oncogene*, 22(27):4205-11 (2003).
Perl et al., *Nature*, 392(6672):190-3 (1998).
Poser et al., *J Biol Chem*, 276(27):24661-6 (2001).
Rodrigo et al., *Exp. Cell Res.*, 248(2):358-371 (1999).
Rosivatz et al., *Am. J. Pathol.*, 161(5):1881-1891 (2002).
Roy et al., *Carcinogenesis*, 23(1): 201-5 (2002).
Saito et al., *Am J Pathol.*, 159(6): 2117-24 (2001).
Sharov et al., *J Invest Dermatol.*, 120(1): 27-35 (2003).
Stein, D., et al., *Antisense Nucleic Acid Drug Dev.*, 7(3):151-7 (1997).
Takeichi et al., *Curr Opin. Cell Biol.*, 5(5):806-811 (1993).
Tan et al., *Oncogene*, 20(1):133-140 (2001).
Toulme, J. J., R. L. Tinevez, et al. (1996). "Targeting RNA structures by antisense oligonucleotides." *Biochimie*, 78(7):663-73.
Wali et al., *Cancer Epidemiol. Biomarkers Prev.*, 11(12):1653-1662 (2002).
Williams et al., *Br. J. Rheumatology*, 35(8):719-724 (1996).
Yanez-Mo et al., *N. England J. Med.*, 348(5):403-413(2003).
Yokoyama et al., *Oral Oncology*, 37(1):65-71 (2001).
Young et al., *Embo J.*, 22(21):5723-5733 (2003).
Roy et al., *Digestive Diseases and Sciences*, 50(1):42-46 (2005).

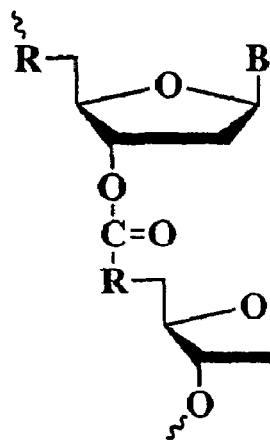
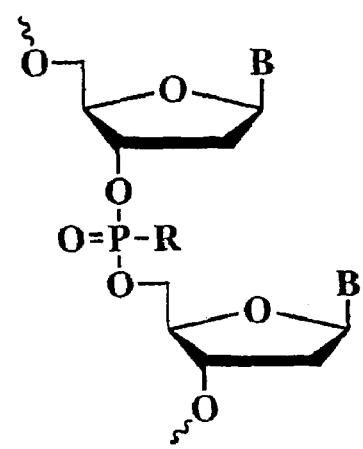
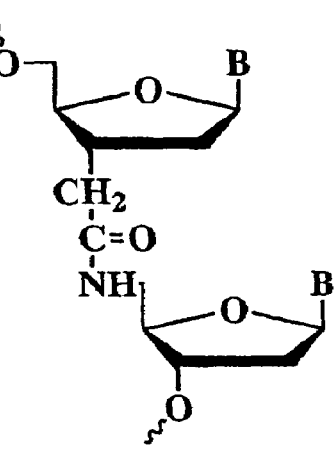
Fig. 3A            Fig. 3B            Fig. 3C
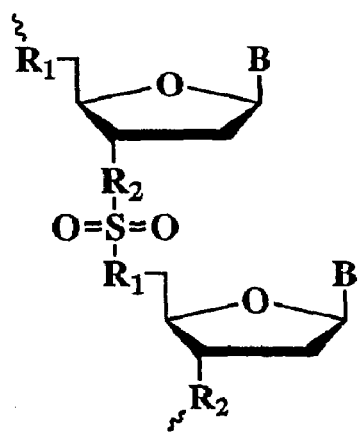
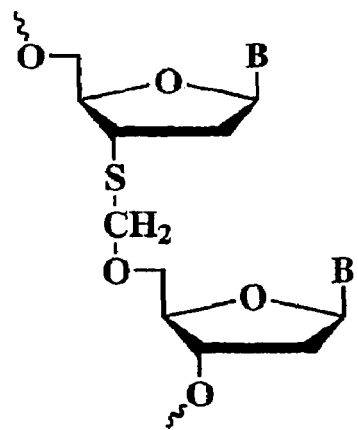
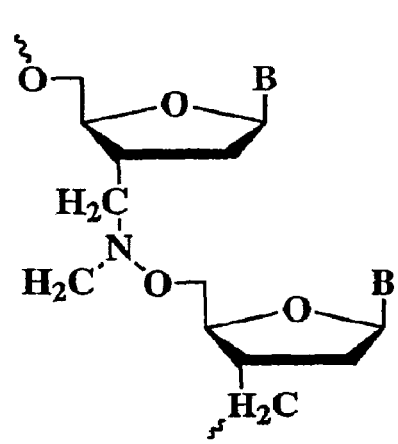
Fig. 3D            Fig. 3E            Fig. 3F
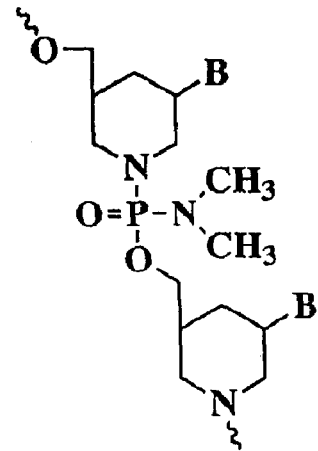
Fig. 3G

SEQUENCE LISTING

<160> NUMBER OF SEQ ID NOS: 24

<210> SEQ ID NO 1
<211> LENGTH: 19
<212> TYPE: DNA
<213> ORGANISM: Artificial Sequence
<220> FEATURE:
<223> OTHER INFORMATION: Synthetic

<400> SEQUENCE: 1
ggccaacatg ccgcgctcc                                               19

<210> SEQ ID NO 2
<211> LENGTH: 21
<212> TYPE: DNA
<213> ORGANISM: Artificial Sequence
<220> FEATURE:
<223> OTHER INFORMATION: Synthetic

<400> SEQUENCE: 2
cgaccccagt gcctcgacca c                                            21

<210> SEQ ID NO 3
<211> LENGTH: 21
<212> TYPE: DNA
<213> ORGANISM: Artificial Sequence
<220> FEATURE:
<223> OTHER INFORMATION: Synthetic

<400> SEQUENCE: 3
ccagtgcctc gaccactatg c                                            21

<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
cctcgaccac tatgccgcgc                                              20

<210> SEQ ID NO 5
<211> LENGTH: 19
<212> TYPE: DNA
<213> ORGANISM: Artificial Sequence
<220> FEATURE:
<223> OTHER INFORMATION: Synthetic

<400> SEQUENCE: 5
cgaccactat gccgcgctc                                        19

<210> SEQ ID NO 6
<211> LENGTH: 21
<212> TYPE: DNA
<213> ORGANISM: Artificial Sequence
<220> FEATURE:
<223> OTHER INFORMATION: Synthetic

<400> SEQUENCE: 6
ccgcgctctt tcctcgtcag g                                     21

<210> SEQ ID NO 7
<211> LENGTH: 21
<212> TYPE: DNA
<213> ORGANISM: Artificial Sequence
<220> FEATURE:
<223> OTHER INFORMATION: Synthetic

<400> SEQUENCE: 7
caggactcta atccaggtgc g                                     21

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
ctccctcaga gtttaccttc                                       20

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
cggacccaca ctggtacgtg                                       20

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
ctctccccag gcgagaagcc                                       20

<210> SEQ ID NO 11
<211> LENGTH: 19
<212> TYPE: DNA
<213> ORGANISM: Artificial Sequence
<220> FEATURE:

<223> OTHER INFORMATION: Synthetic

<400> SEQUENCE: 11
ggagcgcggc atgttggcc                                                       19

<210> SEQ ID NO 12
<211> LENGTH: 21
<212> TYPE: DNA
<213> ORGANISM: Artificial Sequence
<220> FEATURE:
<223> OTHER INFORMATION: Synthetic

<400> SEQUENCE: 12
gtggtcgagg cactggggtc g                                                    21

<210> SEQ ID NO 13
<211> LENGTH: 21
<212> TYPE: DNA
<213> ORGANISM: Artificial Sequence
<220> FEATURE:
<223> OTHER INFORMATION: Synthetic

<400> SEQUENCE: 13
gcatagtggt cgaggcactg g                                                    21

<210> SEQ ID NO 14
<211> LENGTH: 20
<212> TYPE: DNA
<213> ORGANISM: Artificial Sequence
<220> FEATURE:
<223> OTHER INFORMATION: Synthetic

<400> SEQUENCE: 14
gcgcggcata gtggtcgagg                                                      20

<210> SEQ ID NO 15
<211> LENGTH: 19
<212> TYPE: DNA
<213> ORGANISM: Artificial Sequence
<220> FEATURE:
<223> OTHER INFORMATION: Synthetic

<400> SEQUENCE: 15
gagcgcggca tagtggtcg                                                       19

<210> SEQ ID NO 16
<211> LENGTH: 21
<212> TYPE: DNA
<213> ORGANISM: Artificial Sequence
<220> FEATURE:
<223> OTHER INFORMATION: Synthetic

<400> SEQUENCE: 16
cctgacgagg aaagagcgcg g                                                    21

<210> SEQ ID NO 17
<211> LENGTH: 21
<212> TYPE: DNA
<213> ORGANISM: Artificial Sequence
<220> FEATURE:
<223> OTHER INFORMATION: Synthetic

<400> SEQUENCE: 17
cgcacctgga ttagagtcct g                                                    21

```
<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18
gaaggtaaac tctgagggag                                                     20

<210> SEQ ID NO 19
<211> LENGTH: 20
<212> TYPE: DNA
<213> ORGANISM: Artificial Sequence
<220> FEATURE:
<223> OTHER INFORMATION: Synthetic

<400> SEQUENCE: 19
cacgtaccag tgtgggtccg                                                     20

<210> SEQ ID NO 20
<211> LENGTH: 20
<212> TYPE: DNA
<213> ORGANISM: Artificial Sequence
<220> FEATURE:
<223> OTHER INFORMATION: Synthetic

<400> SEQUENCE: 20
ggcttctcgc ctggggagag                                                     20

<210> SEQ ID NO 21
<211> LENGTH: 6258
<212> TYPE: DNA
<213> ORGANISM: Homo sapiens

<400> SEQUENCE: 21 cccaccccc accaccccc ggagtactta agggagttgg cggcgctgct gcattcattg           60
cgccgcggca cggcctagcg agtggttctt ctgcgctact gctgcgcgaa tcggcgaccc        120
cagtgcctcg accactatgc cgcgctcttt cctcgtcagg aagccctccg accccaatcg        180
gaagcctaac tacagcgagc tgcaggactc taatccaggt gcgttggagg ggttctgggc        240
tccaggaggt ttgggggaga caggcgaagg ctgcgtgggg ggcacctgag ggaggcggcc        300
tgcctgagcc aggatcgagt cacaggatgt tttgtggacc attgcgggct cgggagaccg        360
ggcaagtggg tccccagttc cggggatctg tctgggtggt tggggagtg ccgtgtagag         420 ggcagggtc ttcagcttgg ggggcctttg tagccggcga gaggcggagg agctccgcaa        480
gaggggaagg agaggaggcc tgtgtcagga gggccctctg gacgctgctg ggagagtcc         540 ggagtccaga gggttgaggg gaggggtggg gagacgagat gtgtgtgagg aggggattg         600 gggcagggtg gtggctccgg ggctgggatg atgggttct ggcctcaggc tggagactgg         660
ggacttagga gagggagatc aggaaatgac ctccttcaac tgggggtcct acgtgtgaga        720
gactcagatt gggtgacctg gcgaggagg caggaacct ggtctgtcct gtggataatt          780 ttttttgatct aattatgtat tgagaatcgg ccccacccag cccctggcca gcggtgggct      840
catgtttgtt gattgagtga atgatttaat taacgcctga ctctgctttt tctccctcag       900
agtttacctt ccagcagccc tacgaccagg cccacctgct ggcagccatc ccacctccgg       960
agatcctcaa ccccaccgcc tcgctgccaa tgctcatctg ggactctgtc ctggcgcccc      1020
aagcccagcc aattgcctgg gcctcccttc ggctccagga gagtcccagg gtggcagagc      1080
```

```
tgacctccct gtcagatgag gacagtggga aaggctccca gcccccagc ccaccctcac    1140 cggctccttc gtccttctcc tctacttcag tctcttcctt ggaggccgag gcctatgctg    1200
ccttcccagg cttgggccaa gtgcccaagc agctggccca gctctctgag gccaaggatc    1260
tccaggctcg aaaggccttc aactgcaaat actgcaacaa ggaataccte agcctgggtg    1320 ccctcaagat gcacatccga agccacacgc tgccctgcgt ctgcggaacc tgcgggaagg    1380
ccttctctag gccctggctg ctacaaggcc atgtccggac ccacactggt acgtgcccct    1440
ccaggcgccc ccaccgttgc tctctctggc agcttttgtg aatctgggct gctgttctc    1500 attcccaaag ctgtggacac tgaggccccg agtcttctaa cttctagctc aagttccagg    1560
gcctggctct ctggaaacgt ttggcagaaa ctttcttcat cagctaagca gatgggcaaa    1620
gcagacacct tcccaatccc ctgcagcctg tttctcagcc aaatgggtcg gagctggata    1680
tgggaaaggt gcaaccaaca ccttgctgtg ggggccaggt gtgaaggggc cacccggcc    1740 acaccctctc ccgggtccgc cccctcccta gccagacagg atgttgtcag accccccgcc    1800
tggctctgaa tccttctttg agaactttct caaaacttag gctgatgttt ctcttctgtg    1860
agcctcattt tctctatctt tcagatgggc atgagaacag cttttggggt ttctatacag    1920
gctaaatgca ggaatgcata tgggaagcac ctggcaaagt gccggtacct gctaaactct    1980
cacaaaaatg gttccttggc atttgctctg cttccttgct gtgtgacttt gggcaagcaa    2040
cttaacctct ctgagcctta ggggaaaact atgatagcat atgtttaga gagtggctgt    2100 aaaggtggct aatcacttta tagtaattta ttatacccga acggttctca ggtcggcttc    2160
cccaccccca ctgaatccta gcacacagac caggaaacgg catctttggg gcagaaaaca    2220
caatcacgtc ttttgaaaat ttactaaatg tgtaaaaaac tttctggaca tggagaaaag    2280
gtagaacttt ttagaacttg aatggtggca gccactgtgc ctggagctgc tctttggaga    2340
gtgacagttg agggagaaga ttccacaggg ttcaagctgg ccaggttctg ccatttcctg    2400
gcctggcgcc tgacctctga gcggtgaggg ttagtgaggt gtctgggagg actggcaatt    2460
cgcgggcttt attggcatct tattcgacta aggctaccca tttctcttcc ttcgtgcacc    2520
aattgctctg atttttaacat gtaaaggtcc aactgcctgg cctcctgggt gcctgcccag    2580
ctcacagggc tctatttttgg gacagttgaa cccctcaggg tgctgcagtc ctgcctgcct    2640
ctctcacctc ccatctggac attatttttaa tgtaaaggca tggctgagac acagaaatcc    2700
ccttgaaatg tatcattgcg gtcctcattg actcccattg tgtgccttaa tggtgggccc    2760
agtgggtggg ggctgggagg ggtggagcag gtgcatgggg cagcggtgcc cagcacctgt    2820
tccagtcaca gctgctggcc cactgcatgg caggcccctt taatccgggg atatcgcatg    2880
tacagtgccc ccctcggcgc ccttttgtccc cgccggcctg gtgccgattt cacacttgcc    2940
aggagtacca tgaaggcgtc tggggggcga gggatccaag gagtgggggt ctgtgcctcc    3000
tgcgtgtgca cacagccccc gcccccagcc catcatgtcc tagaatgtct ccttcccctt    3060
ttgtttgggt tcaggtctca tcacactttg ggcacttact gtacaggagg gtagtgctca    3120
ggacttcacc aacagccctg ggaagggaag ggaggtgctg tcctaactct ggtcttacaa    3180
atggactcca gccccttttc cagatctcca gagtcagccc ttagttcaca agggtgaact    3240
tacccttctc attcacatga agacttagaa tgcaatcaac aaaccccttca ggcgtggcgt    3300 gtggaggctg ctgagtaatg gcagagtgga gtagtgctca ggcacccctc ccccaatcct    3360
ctatgtcccc caccctttgg agtggcgagt ttccatttct gccccatgag actgagtcca    3420
gctctcaggc gctccataag tccctattga atgcatgggt cccattggag ccatcctctg    3480
```

```
gactctctcc taccctggta gctcagtgtg gcaccctagg cacccaggag gtgatggaat    3540
gaattcactc tcagctctta aattccatcc agcgctggga tttcacaggc gggccctgac    3600
cttgcgggca tatcagactg ggcgtgaggg gattggagaa ttgcatgttt tttaaaaaga    3660
ctattcagta ttatggaata gtgtctagca cttagtagga gctcagtaga ttaaaaaaaa    3720
aattatagac agggtcttgc tttatcgcct aggcttgtct caaactcctg gcttcaagca    3780
atcctgcctc actcggcctc ccagagtgat gggattacaa gcgtgagcca ccacacccag    3840
cctcaataga ttttgtttta atgggttact gttatgacct tttatttgga aaatgctgca    3900
tcccccagaa aaaacaaat caacattatt ggtgttttg gaactatata gcttttggt      3960 tggagcaggg attgttatga ggcatgagtg aggggggcaga ctcctctgag gcctctttaa   4020 ttttttaaaac agacttattt attctctaag ggcttgttga ggatttactg ggcacccagc   4080
tccatgtgca agacttttcc caacacagcc ttggccaggc agatggtgtg tcagggccac    4140
aggtttccgt agcctcttgg gtgatagaaa ggggcccagg ccctgggctg gggctcagaa    4200
gggactcaaa ggaggccctt gcccttatgg gactcagcct gattggagaa cagacaagga    4260
gatttgggat tacagcgcag gaggtgggggt ggtgaggaaa gcaggctgct ggccgggccc   4320
caggagtggc ctaaccagct tggaggtggg ggtggggaag cctcttaagg ctgactctgg    4380 cttttggcccc caacagagta aatcaaggaa tgactccagg actgatggta aggacaccag   4440
tcacgtcctc ccttgactga aggcagtaag ggcagtaggt gaaatcagag gctttggggt   4500
cctgccaggg gaacctgaac atgctacttc tgggcctcag tttcactgtc tctgaaatga    4560
gaccacagta ggatcaagtg acagtaggat gaatcagtaa aggtgttgag tcattgttga    4620
ccacttcgca cgtccctgcg ggatgtggat gagtacccta ccttctgtca cttatcaacc    4680
cctatgagtg gggggtgaat agccccattt tacaggtggg aaaatggagg ctcagagaag    4740
ccagacaact tgctcagagt tgcacagtgg gaagcagcag agctccgtca ggtcccggcc    4800
tttggaccct ggctgtgtgt tgacggagg cctggctttc ctgggatcat gggattcttt     4860
cagggtttgg ggtatgcggg gagggattcc catcactgcc agccgttgtc ccacggctca    4920
ctcggccttt ctggcgttct ctccccaggc gagaagccct tctcctgtcc ccactgcagc    4980
cgtgccttcg ctgaccgctc caacctgcgg gccacctcc agacccactc agatgtcaag     5040
aagtaccagt gccaggcgtg tgctcggacc ttctcccgaa tgtccctgct ccacaagcac    5100
caagagtccg gctgctcagg atgtccccgc tgaccctcga ggctccctct tcctctccat    5160 acctgccccct gcctgacagc cttcccagc tccagcagga aggacccac atccttctca    5220 ctgccatgga attcctcct gagtgcccca cttctggcca catcagcccc acaggacttt   5280
gatgaagacc attttctggt tctgtgtcct ctgcctgggc tctggaagag gccttcccgt    5340
ggccatttct gtggagggag ggcagctggc ccccagccct gggggattcc tgagctggcc    5400
tgtctgcgtg ggttttttgta tccagagctg tttggataca gctgctttga gctacaggac   5460
aaaggctgac agactcactg ggaagctccc accccactca ggggacccca ctcccctcac    5520
acaccccccc ccacaaggaa ccctcaggcc accctccacg aggtgtgact aactatgcaa    5580
```

```
taatccaccc ccaggtgcag ccccagggcc tgcggaggcg gtggcagact agagtctgag    5640
atgccccgag cccaggcagc tatttcagcc tcctgtttgg tggggtggca cctgtttccc    5700
gggcaattta acaatgtctg aaaagggact gtgagtaatg gctgtcactt gtcggggcc    5760 caagtggggt gctctggtct gaccgatgtg tctcccagaa ctattctggg ggcccgacag    5820
gtgggcctgg gaggaagatg tttacatttt taaaggtaca ctggtattta tatttcaaac    5880
attttgtatc aaggaaacgt tttgtatagt tatatgtaca gtttattgat attcaataaa    5940
gcagttaatt tatatattaa aaagtctttg gtgtcataga ggagtgggta ttttgaaagg    6000
tctttggtaa gggaggaggg gacaggaatt cctgaagctt agatatttct gacacagcct    6060
taaatcttgt ccttggaaac atcatagggc tttggagtcc tgggtgtcac tgtcagggac    6120
cttatgagac tgggttttcc cgttggcctg ggtgtcctgt ctgctgctgt ttgggtgagc    6180
cagcggcatc catacgagct cttcactata cactgtggct ttttactttc tcgttcttga    6240
attttgaagt tgatctgg                                                  6258
```

```
<210> SEQ ID NO 22
<211> LENGTH: 12
<212> TYPE: PRT
<213> ORGANISM: Artificial Sequence
<220> FEATURE:
<223> OTHER INFORMATION: Synthetic

<400> SEQUENCE: 22

Arg Arg Arg Arg Arg Arg Arg Arg Arg Phe Phe Cys
 1               5                   10

<210> SEQ ID NO 23
<211> LENGTH: 12
<212> TYPE: PRT
<213> ORGANISM: Artificial Sequence
<220> FEATURE:
<223> OTHER INFORMATION: Synthetic

<400> SEQUENCE: 23

Arg Arg Arg Arg Arg Phe Phe Arg Arg Arg Arg Cys
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (2)..(11)
<223> OTHER INFORMATION: Xaa = Ahx

<400> SEQUENCE: 24

Arg Xaa Arg Arg Xaa Arg Arg Xaa Arg Arg Xaa Arg
1               5                   10
```

ANTISENSE COMPOSITION AND METHOD FOR TREATING CANCER

This patent application claims priority to U.S. provisional patent application No. 60/552,835 filed on Mar. 12, 2004, which is incorporated herein in its entirety by reference.

FIELD OF THE INVENTION

This invention relates to compounds and methods for treating cancer, in particular, for suppressing or inhibiting carcinogenesis in a human subject by administering an antisense oligomer to SNAIL.

REFERENCES

RAgrawal, S., S. H. Mayrand, et al. (1990). "Site-specific excision from RNA by RNase H and mixed-phosphate-backbone oligodeoxynucleotides." *Proc Natl Acad Sci USA* 87(4): 1401-5.

Barker, N. and H. Clevers (2001). "Tumor environment: a potent driving force in colorectal cancer?" *Trends Mol Med* 7(12): 535-7.

Batlle, E., E. Sancho, et al. (2000). "The transcription factor snail is a repressor of E-cadherin gene expression in epithelial tumour cells." *Nat Cell Biol* 2(2): 84-9.

Bennett, M. R. and S. M. Schwartz (1995). "Antisense therapy for angioplasty restenosis. Some critical considerations." *Circulation* 92(7): 1981-93.

Birchmeier, W. and J. Behrens (1994). "Cadherin expression in carcinomas: role in the formation of cell junctions and the prevention of invasiveness." *Biochim Biophys Acta* 1198(1): 11-26.

Blanco, M. J., G. Moreno-Bueno, et al. (2002). "Correlation of Snail expression with histological grade and lymph node status in breast carcinomas." *Oncogene* 21(20): 3241-6.

Blommers, M. J., U. Pieles, et al. (1994). "An approach to the structure determination of nucleic acid analogues hybridized to RNA. NMR studies of a duplex between 2'-OMe RNA and an oligonucleotide containing a single amide backbone modification." *Nucleic Acids Res* 22(20): 4187-94.

Bonham, M. A., S. Brown, et al. (1995). "An assessment of the antisense properties of RNase H-competent and steric-blocking oligomers." *Nucleic Acids Res* 23(7): 1197-203.

Boudvillain, M., M. Guerin, et al. (1997). "Transplatin-modified oligo(2'-O-methyl ribonucleotide)s: a new tool for selective modulation of gene expression." *Biochemistry* 36(10): 2925-31.

Bussemakers, M. J., L. A. Giroldi, et al. (1994). "Transcriptional regulation of the human E-cadherin gene in human prostate cancer cell lines: characterization of the human E-cadherin gene promoter." *Biochem Biophys Res Commun* 203(2): 1284-90.

Cano, A., M. A. Perez-Moreno, et al. (2000). "The transcription factor snail controls epithelial-mesenchymal transitions by repressing E-cadherin expression." *Nat Cell Biol* 2(2): 76-83.

Carver, E. A., R. Jiang, et al. (2001). "The mouse snail gene encodes a key regulator of the epithelial-mesenchymal transition." *Mol Cell Biol* 21(23): 8184-8.

Cavallaro, U., B. Schaffhauser, et al. (2002). "Cadherins and the tumour progression: is it all in a switch?" *Cancer Lett* 176(2): 123-8.

Corpet, D. E. and F. Pierre (2003). "Point: From animal models to prevention of colon cancer. Systematic review of chemoprevention in min mice and choice of the model system." *Cancer Epidemiol Biomarkers Prev* 12(5): 391-400.

Dagle, J. M., J. L. Littig, et al. (2000). "Targeted elimination of zygotic messages in *Xenopus laevis* embryos by modified oligonucleotides possessing terminal cationic linkages." *Nucleic Acids Res* 28(10): 2153-7.

Ding, D., S. M. Grayaznov, et al. (1996). "An oligodeoxyribonucleotide N3'-->P5' phosphoramidate duplex forms an A-type helix in solution." *Nucleic Acids Res* 24(2): 354-60.

Fearon, E. R. (2003). "Connecting estrogen receptor function, transcriptional repression, and E-cadherin expression in breast cancer." *Cancer Cell* 3(4): 307-10.

Felgner, P. L., T. R. Gadek, et al. (1987). "Lipofection: a highly efficient, lipid-mediated DNA-transfection procedure." *Proc Natl Acad Sci USA* 84(21): 7413-7.

Gait, M. J., A. S. Jones, et al. (1974). "Synthetic-analogues of polynucleotides XII. Synthesis of thymidine derivatives containing an oxyacetamido- or an oxyformamido-linkage instead of a phosphodiester group." *J Chem Soc [Perkin 1]* (14): 1684-6.

Gee, J. E., I. Robbins, et al. (1998). "Assessment of high-affinity hybridization, RNase H cleavage, and covalent linkage in translation arrest by antisense oligonucleotides." *Antisense Nucleic Acid Drug Dev* 8(2): 103-11.

Giroldi, L. A., P. P. Bringuier, et al. (1997). "Role of E boxes in the repression of E-cadherin expression." *Biochem Biophys Res Commun* 241(2): 453-8.

Grille, S. J., A. Bellacosa, et al. (2003). "The protein kinase Akt induces epithelial mesenchymal transition and promotes enhanced motility and invasiveness of squamous cell carcinoma lines." *Cancer Res* 63(9): 2172-8.

Hajra, K. M., D. Y. Chen, et al. (2002). "The SLUG zinc-finger protein represses E-cadherin in breast cancer." *Cancer Res* 62(6): 1613-8.

Hemavathy, K., S. I. Ashraf, et al. (2000). "Snail/slug family of repressors: slowly going into the fast lane of development and cancer." *Gene* 257(1): 1-12.

Hirohashi, S. (1998). "Inactivation of the E-cadherin-mediated cell adhesion system in human cancers." *Am J Pathol* 153(2): 333-9.

Hudziak, R. M., J. Summerton, et al. (2000). "Antiproliferative effects of steric blocking phosphorodiamidate morpholino antisense agents directed against c-myc." *Antisense Nucleic Acid Drug Dev* 10(3): 163-76.

Jiao, W., K. Miyazaki, et al. (2002). "Inverse correlation between E-cadherin and Snail expression in hepatocellular carcinoma cell lines in vitro and in vivo." *Br J Cancer* 86(1): 98-101.

Kinzler, K. W. and B. Vogelstein (1996). "Lessons from hereditary colorectal cancer." *Cell* 87(2): 159-70.

Kishimoto, Y., N. Takata, et al. (2000). "Sulindac and a cyclooxygenase-2 inhibitor, etodolac, increase APC mRNA in the colon of rats treated with azoxymethane." *Gut* 47(6): 812-9.

Lappalainen, K., A. Urtti, et al. (1994). "Cationic liposomes improve stability and intracellular delivery of antisense oligonucleotides into CaSki cells." *Biochim Biophys Acta* 1196(2): 201-8.

Lesnikowski, Z. J., M. Jaworska, et al. (1990). "Octa(thymidine methanephosphonates) of partially defined stereochemistry: synthesis and effect of chirality at phosphorus on binding to pentadecadeoxyriboadenylic acid." *Nucleic Acids Res* 18(8): 2109-15.

Llorens, A., I. Rodrigo, et al. (1998). "Down-regulation of E-cadherin in mouse skin carcinoma cells enhances a migratory and invasive phenotype linked to matrix metalloproteinase-9 gelatinase expression." *Lab Invest* 78(9): 1131-42.

Lou, X., K. L. Garrett, et al. (2001). "Synthetic hydrogels as carriers in antisense therapy: preliminary evaluation of an oligodeoxynucleotide covalent conjugate with a copolymer of 1-vinyl-2-pyrrolidinone and 2-hydroxyethyl methacrylate." *J Biomater Appl* 15(4): 307-20.

Mertes, M. P. and E. A. Coats (1969). "Synthesis of carbonate analogs of dinucleosides. 3'-Thymidinyl 5'-thymidinyl carbonate, 3'-thymidinyl 5'-(5-fluoro-2'-deoxyuridinyl)carbonate, and 3'-(5-fluoro-2'-deoxyuridinyl) 5'-thymidinyl carbonate." *J Med Chem* 12(1): 154-7.

Moser, A. R., H. C. Pitot, et al. (1990). "A dominant mutation that predisposes to multiple intestinal neoplasia in the mouse." *Science* 247(4940): 322-4.

Nieto, M. A. (2002). "The snail superfamily of zinc-finger transcription factors." *Nat Rev Mol Cell Biol* 3(3): 155-66.

Nyormoi, O. and M. Bar-Eli (2003). "Transcriptional regulation of metastasis-related genes in human melanoma." *Clin Exp Metastasis* 20(3): 251-63.

Perez-Losada, J., M. Sanchez-Martin, et al. (2003). "The radioresistance biological function of the SCF/kit signaling pathway is mediated by the zinc-finger transcription factor Slug." *Oncogene* 22(27): 4205-11.

Perl, A. K., P. Wilgenbus, et al. (1998). "A causal role for E-cadherin in the transition from adenoma to carcinoma." *Nature* 392(6672): 190-3.

Poser, I., D. Dominguez, et al. (2001). "Loss of E-cadherin expression in melanoma cells involves up-regulation of the transcriptional repressor Snail." *J Biol Chem* 276(27): 24661-6.

Rodrigo, I., A. C. Cato, et al. (1999). "Regulation of E-cadherin gene expression during tumor progression: the role of a new Ets-binding site and the E-pal element." *Exp Cell Res* 248(2): 358-71.

Rosivatz, E., I. Becker, et al. (2002). "Differential expression of the epithelial-mesenchymal transition regulators snail, SIP1, and twist in gastric cancer." *Am J Pathol* 161(5): 1881-91.

Roy, H. K., B. F. Olusola, et al. (2002). "AKT proto-oncogene overexpression is an early event during sporadic colon carcinogenesis." *Carcinogenesis* 23(1): 201-5.

Saito, T., Y. Oda, et al. (2001). "E-cadherin gene mutations frequently occur in synovial sarcoma as a determinant of histological features." *Am J Pathol* 159(6): 2117-24.

Sharov, A. A., G. Z. Li, et al. (2003). "Fas and c-kit are involved in the control of hair follicle melanocyte apoptosis and migration in chemotherapy-induced hair loss." *J Invest Dermatol* 120(1): 27-35.

Stein, D., E. Foster, et al. (1997). "A specificity comparison of four antisense types: morpholino, 2'-O-methyl RNA, DNA, and phosphorothioate DNA." *Antisense Nucleic Acid Drug Dev* 7(3): 151-7.

Takeichi, M. (1993). "Cadherins in cancer: implications for invasion and metastasis." *Curr Opin Cell Biol* 5(5): 806-11.

Tan, C., P. Costello, et al. (2001). "Inhibition of integrin linked kinase (ILK) suppresses beta-catenin-Lef/Tcf-dependent transcription and expression of the E-cadherin repressor, snail, in APC-/- human colon carcinoma cells." *Oncogene* 20(1): 133-40.

Toulme, J. J., R. L. Tinevez, et al. (1996). "Targeting RNA structures by antisense oligonucleotides." *Biochimie* 78(7): 663-73.

Wali, R. K., S. Khare, et al. (2002). "Ursodeoxycholic acid and F(6)-D(3) inhibit aberrant crypt proliferation in the rat azoxymethane model of colon cancer: roles of cyclin Dl and E-cadherin." *Cancer Epidemiol Biomarkers Prev* 11(12): 1653-62.

Williams, A. S., J. P. Camilleri, et al. (1996). "A single intra-articular injection of liposomally conjugated methotrexate suppresses joint inflammation in rat antigen-induced arthritis." *Br J Rheumatol* 35(8): 719-24.

Yanez-Mo, M., E. Lara-Pezzi, et al. (2003). "Peritoneal dialysis and epithelial-to-mesenchymal transition of mesothelial cells." *N Enql J Med* 348(5): 403-13.

Yokoyama, K., N. Kamata, et al. (2001). "Reverse correlation of E-cadherin and snail expression in oral squamous cell carcinoma cells in vitro." *Oral Oncol* 37(1): 65-71.

Young, P., O. Boussadia, et al. (2003). "E-cadherin controls adherens junctions in the epidermis and the renewal of hair follicles." *Embo J* 22(21): 5723-33.

BACKGROUND OF THE INVENTION

The National Cancer Institute estimates 1,334,100 new cancer cases are expected to be diagnosed in the United States during 2003 and 556,500 people will die from the disease. Prostate and lung cancers are the leading cause of death in men while breast cancer and lung cancer are the leading cause of death in women. It is also estimated that 8.9 million Americans with a history of cancer were alive in 1999. Worldwide the mortality statistics are more dismal due, in part, to the lack of early diagnosis opportunities available in developing countries.

Despite advances in cancer treatment strategies, lack of efficacy and/or significant side effects due to the toxicity of currently used chemotherapeutic agents remain a problem. Drug toxicity can be severe enough to result in life threatening situations requiring administration of drugs to counteract side effects, and may result in the reduction or discontinuation of the chemotherapeutic agent. One of the major limitations to clinical use of cancer therapeutic agents is the development of resistance to the treatment. These drawbacks to current therapies impact negatively on the patient's treatment and quality of life and exemplify the need for new anticancer therapies.

The development of tumor malignancy, and particular, the progression from a primary tumor to a metastatic cancer, may involve alterations in a tumor cell's ability to adhere and communicate with neighboring cells and with its extracellular environment. Intercellular adhesion of epithelial cells during embryonic development and in adult tissues is mediated by the protein E-cadherin. E-cadherin is also implicated in the phenotypic transformation observed in epithelial tumors during their progression into invasive tumors. Expression of the protein E-cadherin may be reduced or abolished in the process of tumor cell invasion and this loss is associated with the progression to tumor malignancy. The modification of E-cadherin has also been associated with de-differentiation and greater aggressiveness of tumors (Takeichi 1993; Birchmeier and Behrens 1994) and has been implicated in the transition from adenomas to invasive carcinomas (Perl, Wilgenbus et al. 1998). These observations support the suggestion that the E-cadherin gene is a tumor invasion suppressor gene (Llorens, Rodrigo et al. 1998).

It would therefore be desirable to develop a therapy that would prevent or suppress the progression of a tumor, e.g., solid tumor, to an invasive or metastatic state, through a mechanism that acts to maintain expression of the protein E-cadherin in cancer cells.

It would be further desirable to develop a therapy that can be used in conjunction with conventional chemotherapeutic agents to control the growth and spread of cancer cells in a subject.

SUMMARY OF THE INVENTION

In one aspect, the invention includes an antisense composition that comprises a substantially uncharged antisense compound (i) having a nuclease-resistant backbone, (ii) capable of uptake by target cancer cells in the subject, (iii) containing between 10-40 nucleotide bases, and (iv) having and a base sequence effective to hybridize to a region of processed or preprocessed human SNAIL RNA transcript, identified, in its preprocessed form, by SEQ ID NO:21. The compound is effective to form a base-paired heteroduplex structure composed of human SNAIL RNA transcript and the oligonucleotide compound, and characterized by a Tm of dissociation of at least 45° C.

The compound may be composed of morpholino subunits and phosphorus-containing intersubunit linkages joining a morpholino nitrogen of one subunit to a 5' exocyclic carbon of an adjacent subunit. In an exemplary compound, the morpholino subunits are joined by phosphorodiamidate linkages, in accordance with the structure:

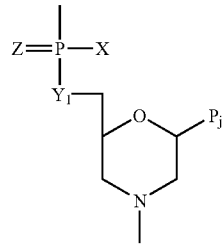

where $Y_1$=O, Z=O, Pj is a purine or pyrimidine base-pairing moiety effective to bind, by base-specific hydrogen bonding, to a base in a polynucleotide, and X is alkyl, alkoxy, thioalkoxy, amino or alkyl amino, including dialkylamino.

The composition may be a conjugate of the compound and an arginine-rich polypeptide effective to promote uptake of the compound into target cells. The arginine-rich peptide may have one of the sequences identified as SEQ ID NOS:22-24. The peptide may be covalently coupled at its C terminus to the 3' end of the antisense compound.

In one general embodiment, the compound is effective to target the start site of the processed SNAIL transcript, and has a base sequence that is complementary to a target region containing at least 12 contiguous bases in a processed human SNAIL transcript, and which includes at least 6 contiguous bases of one of the sequences identified as SEQ ID NOS:1-6. Exemplary compounds of this embodiment have one of the sequences identified as SEQ ID NOS: 11-16.

In another general embodiment, the compound is effective to target a splice site of preprocessed human SNAIL transcript, and has a base sequence that is complementary to a target region containing at least 12 contiguous bases in a preprocessed human SNAIL transcript, and which includes at least 6 contiguous bases of one of the sequences identified as SEQ ID NOS:7-10. Exemplary compounds of this embodiment have one of the sequences identified by SEQ ID NOS: 17-20.

For use in inhibiting the progression of a cancer to an invasive, the composition may further include a pharmaceutically acceptable vehicle for administering the compound to the patient. For use in preventing the transdifferentiation of peritoneal mesothelial cells and failure of ultrafiltration in patients undergoing peritoneal dialysis, the composition may further include a sterile vehicle suitable for addition of the compound to dialysis fluid.

In another aspect, the invention includes a method of treating cancer in a subject, by administering to the subject, a therapeutically effective dose of a substantially uncharged antisense compound of the type described above. Administering the compound is effective to form within target cancer cells in the subject, a base-paired heteroduplex structure composed of human SNAIL RNA transcript and the oligonucleotide compound, where this structure is characterized by a Tm of dissociation of at least 45° C. The amount of compound administered is sufficient to inhibit SNAIL expression in target cancer cells, thereby to inhibit the progression of the patient's cancer to a more invasive, metastatic state. Various compound and composition embodiments discussed above apply to the method.

In still another aspect, the invention includes a method for inhibiting or preventing the transdifferentiation of peritoneal mesothelial cells and failure of ultrafiltration in a patient undergoing peritoneal dialysis. The method involves adding to the dialysis fluid of the patient, during a peritoneal dialysis procedure, a sterile solution of the antisense compound described above. Including the compound in the dialysis fluid is effective to form within target mesothelial cells in the patient, a base-paired heteroduplex structure composed of human SNAIL RNA transcript and the oligonucleotide compound, where this structure is characterized by a Tm of dissociation of at least 45° C. The amount of compound added is sufficient to inhibit SNAIL expression in target mesothelial cells, thereby to inhibit or prevent the transdifferentiation of peritoneal mesothelial cells in the patient. Various compound and composition embodiments discussed above apply to the method.

These and other objects and features of the invention will become more fully apparent when the following detailed description is read in conjunction with the accompanying figures and examples.

BRIEF DESCRIPTION OF THE FIGURES

FIGS. 3A-3G show examples of uncharged linkage types in oligonucleotide analogs.

DETAILED DESCRIPTION OF THE INVENTION

I. Definitions

The terms below, as used herein, have the following meanings, unless indicated otherwise:

As used herein, the terms "compound", "agent", "oligomer" and "oligonucleotide" may be used interchangeably with respect to the antisense oligonucleotides of the invention.

As used herein, the terms "antisense oligonucleotide" and "antisense oligomer" are used interchangeably and refer to a sequence of nucleotide bases and a subunit-to-subunit backbone that allows the antisense oligomer to hybridize to a target sequence in an RNA by Watson-Crick base pairing, to form an RNA:oligomer heteroduplex within the target sequence. The oligomer may have exact sequence complementarity to the target sequence or near complementarity. Such antisense oligomers may block or inhibit translation of the mRNA containing the target sequence, or inhibit gene transcription, may bind to double-stranded or single stranded sequences, and may be said to be "directed to" a sequence with which it hybridizes. Exemplary structures for antisense oligonucleotides for use in the invention include the β-morpholino subunit types shown in FIGS. 1A-1D. It will be appreciated that a polymer may contain more than one linkage type.

Figure 1A:
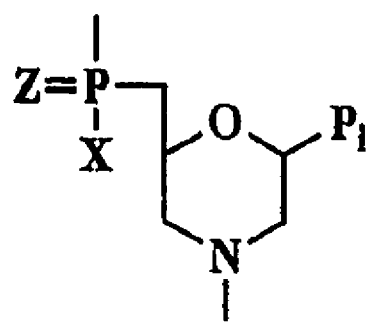
FIGS. 1A-1D show preferred morpholino-type subunits having 5-atom (A), six-atom (B) and seven-atom (C-D) linking groups suitable for forming polymers.
Figure 2A:
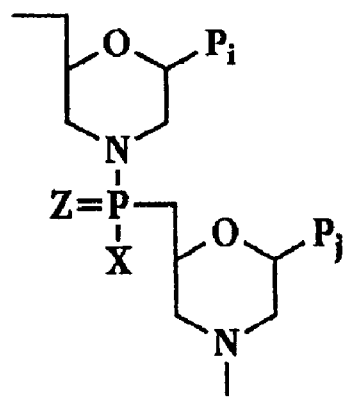
FIGS. 2A-D show the repeating subunit segment of exemplary morpholino oligonucleotides, designated A through D, constructed using subunits A-D, respectively, of FIG. 1.

The subunit of FIG. 1A contains a 1-atom phosphorous-containing linkage which forms the five atom repeating-unit backbone shown in FIG. 2A, where the morpholino rings are linked by a 1-atom phosphonamide linkage.

Figure 1B:
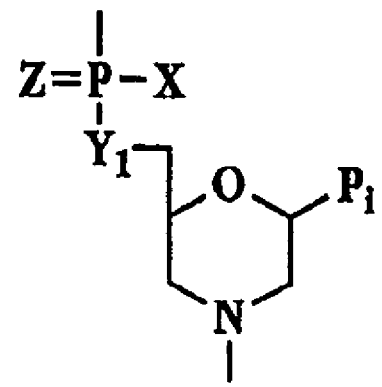
Figure 2B:
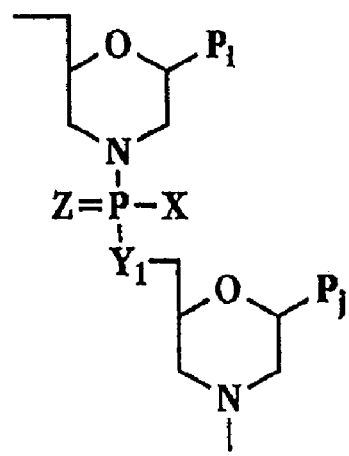

The subunit in FIG. 1B is designed for 6-atom repeating-unit backbones, as shown in FIG. 2B. The atom Y linking the 5' morpholino carbon to the phosphorous group may be sulfur, nitrogen, carbon or, preferably, oxygen. The X moiety pendant from the phosphorous may be any of the following: fluorine; an alkyl or substituted alkyl; an alkoxy or substituted alkoxy; a thioalkoxy or substituted thioalkoxy; or, an unsubstituted, monosubstituted, or disubstituted nitrogen, including cyclic structures.

Figure 1C:
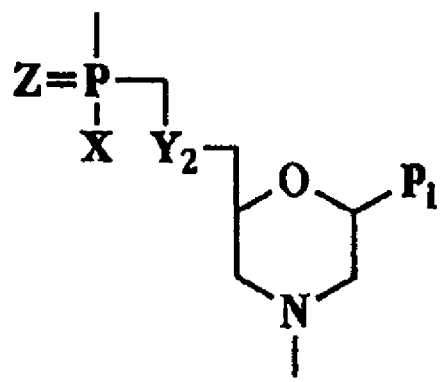
Figure 1D:
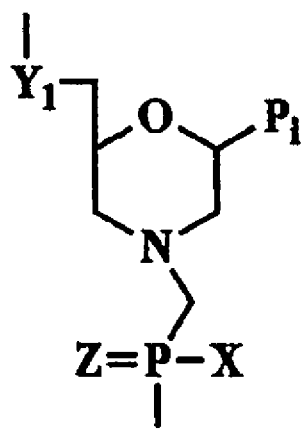
Figure 2C:
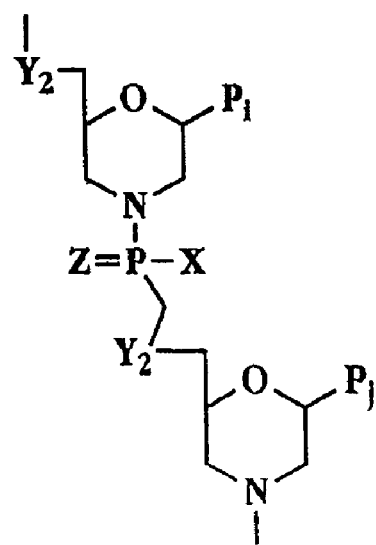
Figure 2D:
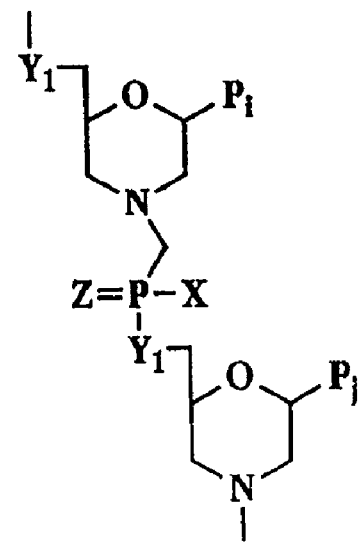

The subunits of FIGS. 1C and 1D are designed for 7-atom unit-length backbones as shown in FIGS. 2C and 2D. In Structure C, the X moiety is as in Structure B and the moiety Y may be a methylene, sulfur, or preferably oxygen. In Structure D, the X and Y moieties are as in Structure B of FIG. 1. In all subunits depicted in FIGS. 1A-1D, Z is O or S, and $P_i$ or $P_j$ is adenine, cytosine, guanine or uracil.

As used herein, a "morpholino oligomer" refers to a polymeric molecule having a backbone which supports bases capable of hydrogen bonding to typical polynucleotides, wherein the polymer lacks a pentose sugar backbone moiety, and more specifically a ribose backbone linked by phosphodiester bonds which is typical of nucleotides and nucleosides, but instead contains a ring nitrogen with coupling through the ring nitrogen. A preferred "morpholino" oligonucleotide is composed of morpholino subunit structures of the form shown in FIG. 2B, where (i) the structures are linked together by phosphorous-containing linkages, one to three atoms long, joining the morpholino nitrogen of one subunit to the 5' exocyclic carbon of an adjacent subunit, and (ii) $P_i$ and $P_j$ are purine or pyrimidine base-pairing moieties effective to bind, by base-specific hydrogen bonding, to a base in a polynucleotide.

This preferred aspect of the invention is illustrated in FIG. 2B, which shows two such subunits joined by a phosphorodiamidate linkage. Morpholino oligonucleotides (including antisense oligomers) are detailed, for example, in co-owned U.S. Pat. Nos. 5,698,685, 5,217,866, 5,142,047, 5,034,506, 5,166,315, 5,185,444, 5,521,063, and 5,506,337, all of which are expressly incorporated by reference herein.

As used herein, a "nuclease-resistant" oligomeric molecule (oligomer) is one whose backbone is not susceptible to nuclease cleavage of a phosphodiester bond. Exemplary nuclease resistant antisense oligomers are oligonucleotide analogs, such as phosphorothioate and phosphate-amine DNA (pnDNA), both of which have a charged backbone, and methyl-phosphonate, morpholino, and peptide nucleic acid (PNA) oligonucleotides, all of which may have uncharged backbones.

As used herein, an oligonucleotide or antisense oligomer "specifically hybridizes" to a target polynucleotide if the oligomer hybridizes to the target under physiological conditions, with a Tm substantially greater than 37° C., preferably at least 50° C., and typically 60° C.-80° C. or higher. Such hybridization preferably corresponds to stringent hybridization conditions, selected to be about 10° C., and preferably about 5° C. lower than the thermal melting point ($T_m$) for the specific sequence at a defined ionic strength and pH. At a given ionic strength and pH, the $T_m$ is the temperature at which 50% of a target sequence hybridizes to a complementary polynucleotide.

Polynucleotides are described as "complementary" to one another when hybridization occurs in an antiparallel configuration between two single-stranded polynucleotides. A double-stranded polynucleotide can be "complementary" to another polynucleotide, if hybridization can occur between one of the strands of the first polynucleotide and the second. Complementarity (the degree that one polynucleotide is complementary with another) is quantifiable in terms of the proportion of bases in opposing strands that are expected to form hydrogen bonds with each other, according to generally accepted base-pairing rules.

As used herein the term "analog" with reference to an oligomer means a substance possessing both structural and chemical properties similar to those of a reference oligomer.

As used herein, a first sequence is an "antisense sequence" with respect to a second sequence if a polynucleotide whose sequence is the first sequence specifically binds to, or specifically hybridizes with, the second polynucleotide sequence under physiological conditions.

As used herein, a "base-specific intracellular binding event involving a target RNA" refers to the sequence specific binding of an oligomer to a target RNA sequence inside a cell. For example, a single-stranded polynucleotide can specifically bind to a single-stranded polynucleotide that is complementary in sequence.

As used herein, "nuclease-resistant heteroduplex" refers to a heteroduplex formed by the binding of an antisense oligomer to its complementary target, which is resistant to in vivo degradation by ubiquitous intracellular and extracellular nucleases.

An agent is "actively taken up by mammalian cells" when the agent can enter the cell by a mechanism other than passive diffusion across the cell membrane. The agent may be transported, for example, by "active transport", referring to transport of agents across a mammalian cell membrane by e.g. an ATP-dependent transport mechanism, or by "facilitated transport", referring to transport of antisense agents across the cell membrane by a transport mechanism that requires binding of the agent to a transport protein, which then facilitates passage of the bound agent across the membrane. For both active and facilitated transport, the oligonucleotide compound preferably has a substantially uncharged backbone, as defined below. Alternatively, the antisense compound may be formulated in a complexed form, such as an agent having an anionic backbone complexed with cationic lipids or liposomes, which can be taken into cells by an endocytotic mechanism. Alternatively, the analog may be conjugated, e.g., at its 5' or 3' end, to an arginine-rich peptide, e.g., the HIV TAT protein, or polyarginine, to facilitate transport into the target host cell, as discussed below.

As used herein, SNAIL refers to the family of transcriptional repressors (including SNAIL, SLUG and SMUC, (Hemavathy, Ashraf et al. 2000)) that has been demonstrated to inhibit tumor suppressor genes in a wide variety of cancers including, but not limited to, breast, hepatocellular, gastric and melanoma.

As used herein, the term "SNAIL antisense oligomer" refers to a nuclease-resistant antisense oligomer having high affinity (ie, which "specifically hybridizes") to a complementary or near-complementary SNAIL nucleic acid sequence.

As used herein, the term "modulating expression" relative to an oligonucleotide refers to the ability of an antisense oligonucleotide (oligomer) to either enhance or reduce the expression of a given protein by interfering with the expression, or translation of RNA. In the case of enhanced protein expression, the antisense oligomer may block expression of a suppressor gene, e.g., a tumor suppressor gene. In the case of reduced protein expression, the antisense oligomer may directly block expression of a given gene, or contribute to the accelerated breakdown of the RNA transcribed from that gene.

As used herein, the terms "tumor" and "cancer" refer to a cell that exhibits a loss of growth control and forms unusually large clones of cells. Tumor or cancer cells generally have lost contact inhibition and may be invasive and/or have the ability to metastasize.

As used herein, "effective amount" relative to an antisense oligomer refers to the amount of antisense oligomer administered to a mammalian subject, either as a single dose or as part of a series of doses and which is effective to inhibit expression of a selected target nucleic acid sequence.

As used herein "treatment" of an individual or a cell is any type of intervention used in an attempt to alter the natural course of the individual or cell. Treatment includes, but is not limited to, administration of e.g., a pharmaceutical composition, and may be performed either prophylactically, or subsequent to the initiation of a pathologic event or contact with an etiologic agent. "Treating cancer" may include inhibiting or blocking cancer cell growth, promoting cancer cell death and/or blocking the progression of solid-tumor, typically primary-tumor cells to a more invasive, metastatic state.

As used herein, "chemotherapeutic agent" refers to any of a number of agents with established or potential use in cancer therapy such as antimetabolites, agents that cause oxidative stress, alkylating agents, natural products, enzymes, therapeutic proteins and other miscellaneous agents.

II. Antisense Oligonucleotides for Use in Practicing the Invention

V. Antisense Oligomers

A. Properties

As will be detailed below, the antisense oligomer of the present invention has a base sequence directed to a targeted portion of the SNAIL mRNA, typically a region at or near the start site of the mRNA or at or near a splice junction in the preprocessed RNA transcript. In addition, the oligomer is able to effectively target patient cancer cells, when administered to the patient. This requirement is met when the oligomer compound (a) has the ability to be actively taken up by mammalian cells, and (b) once taken up, form a duplex with the target mRNA with a $T_m$ greater than about 50° C.

As will be described below, the ability to be taken up by cells requires that the oligomer backbone be substantially uncharged, and, preferably, that the oligomer structure is recognized as a substrate for active or facilitated transport across the cell membrane. The ability of the oligomer to form a stable duplex with the target RNA will also depend on the oligomer backbone, as well as factors noted above, the length and degree of complementarity of the antisense oligomer with respect to the target, the ratio of G:C to A:T base matches, and the positions of any mismatched bases. The ability of the antisense oligomer to resist cellular nucleases promotes survival and ultimate delivery of the agent to the cell cytoplasm.

Below are disclosed methods for testing any given, substantially uncharged backbone for its ability to meet these requirements.

A1. Active or Facilitated Uptake by Cells

The antisense compound may be taken up by patient cancer or tumor cells by facilitated or active transport across the host cell membrane if administered in free (non-complexed) form, or by an endocytotic mechanism if administered in complexed form.

In the case where the agent is administered in free form, the antisense compound should be substantially uncharged, meaning that a majority of its intersubunit linkages are uncharged at physiological pH. Experiments carried out in support of the invention indicate that a small number of net charges, e.g., 1-2 for a 15- to 20-mer oligomer, can in fact enhance cellular uptake of certain oligomers with substantially uncharged backbones. The charges may be carried on the oligomer itself, e.g., in the backbone linkages, or may be terminal charged-group appendages. Preferably, the number of charged linkages is no more than one charged linkage per four uncharged linkages. More preferably, the number is no more than one charged linkage per ten, or no more than one per twenty, uncharged linkages. In one embodiment, the oligomer is fully uncharged.

An oligomer may also contain both negatively and positively charged backbone linkages, as long as opposing charges are present in approximately equal number. Preferably, the oligomer does not include runs of more than 3-5 consecutive subunits of either charge. For example, the oligomer may have a given number of anionic linkages, e.g. phosphorothioate or N3'→P5' phosphoramidate linkages, and a comparable number of cationic linkages, such as N,N-diethylenediamine phosphoramidates (Dagle, Littig et al. 2000). The net charge is preferably neutral or at most 1-2 net charges per oligomer.

In addition to being substantially or fully uncharged, the antisense agent is preferably a substrate for a membrane transporter system (i.e. a membrane protein or proteins) capable of facilitating transport or actively transporting the oligomer across the cell membrane. This feature may be determined by one of a number of tests for oligomer interaction or cell uptake, as follows.

A first test assesses binding at cell surface receptors, by examining the ability of an oligomer compound to displace or be displaced by a selected charged oligomer, e.g., a phosphorothioate oligomer, on a cell surface. The cells are incubated with a given quantity of test oligomer, which is typically fluorescently labeled, at a final oligomer concentration of between about 10-300 nM. Shortly thereafter, e.g., 10-30 minutes (before significant internalization of the test oligomer can occur), the displacing compound is added, in incrementally increasing concentrations. If the test compound is able to bind to a cell surface receptor, the displacing compound will be observed to displace the test compound. If the displacing compound is shown to produce 50% displacement at a concentration of 10× the test compound concentration or less, the test compound is considered to bind at the same recognition site for the cell transport system as the displacing compound.

A second test measures cell transport, by examining the ability of the test compound to transport a labeled reporter, e.g., a fluorescence reporter, into cells. The cells are incubated in the presence of labeled test compound, added at a final concentration between about 10-300 nM. After incubation for 30-120 minutes, the cells are examined, e.g., by microscopy, for intracellular label. The presence of significant intracellular label is evidence that the test compound is transported by facilitated or active transport.

The antisense compound may also be administered in complexed form, where the complexing agent is typically a polymer, e.g., a cationic lipid, polypeptide, or non-biological cationic polymer, having an opposite charge to any net charge on the antisense compound. Methods of forming complexes, including bilayer complexes, between anionic oligonucleotides and cationic lipid or other polymer components, are well known. For example, the liposomal composition Lipofectin® (Felgner, Gadek et al. 1987), containing the cationic lipid DOTMA (N-[1-(2,3-dioleyloxy)propyl]-N,N,N-trimethylammonium chloride) and the neutral phospholipid DOPE (dioleyl phosphatidyl ethanolamine), is widely used. After administration, the complex is taken up by cells through an endocytotic mechanism, typically involving particle encapsulation in endosomal bodies.

The antisense compound may also be administered in conjugated form with an arginine-rich peptide linked to the 5' or 3' end of the antisense oligomer. The peptide is typically 8-16 amino acids and consists of a mixture of arginine, and other amino acids including phenyalanine, cysteine and 6-aminohexanoic acid (Ahx). Exposure of cells to the peptide conjugated oligomer results in enhanced intracellular uptake and delivery to the RNA target. Exemplary arginine-rich peptides are listed as SEQ ID NOS: 22-24.

Alternatively, and according to another aspect of the invention, the requisite properties of oligomers with any given backbone can be confirmed by a simple in vivo test, in which a labeled compound is administered to an animal, and a body fluid sample, taken from the animal several hours after the oligomer is administered, assayed for the presence of heteroduplex with target RNA. This method is detailed in subsection D below.

A2. Substantial Resistance to RNaseH

Two general mechanisms have been proposed to account for inhibition of expression by antisense oligonucleotides (Agrawal, Mayrand et al. 1990; Bonham, Brown et al. 1995; Boudvillain, Guerin et al. 1997). In the first, a heteroduplex formed between the oligonucleotide and the viral RNA acts as a substrate for RNaseH, leading to cleavage of the viral RNA. Oligonucleotides belonging, or proposed to belong, to this class include phosphorothioates, phosphotriesters, and phosphodiesters (unmodified "natural" oligonucleotides). Such compounds expose the viral RNA in an oligomer:RNA duplex structure to hydrolysis by RNaseH, and therefore loss of function.

A second class of oligonucleotide analogs, termed "steric blockers" or, alternatively, "RNaseH inactive" or "RNaseH resistant", have not been observed to act as a substrate for RNaseH, and are believed to act by sterically blocking target RNA nucleocytoplasmic transport, splicing, translation, or replication. This class includes methylphosphonates (Toulme, Tinevez et al. 1996), morpholino oligonucleotides, peptide nucleic acids (PNA's), certain 2'-O-allyl or 2'-O-alkyl modified oligonucleotides (Bonham, Brown et al. 1995), and N3'→P5' phosphoramidates (Ding, Grayaznov et al. 1996; Gee, Robbins et al. 1998).

A test oligomer can be assayed for its RNaseH resistance by forming an RNA:oligomer duplex with the test compound, then incubating the duplex with RNaseH under a standard assay conditions, as described in Stein et al (Stein, Foster et al. 1997). After exposure to RNaseH, the presence or absence of intact duplex can be monitored by gel electrophoresis or mass spectrometry.

A3. In vivo Uptake

In accordance with another aspect of the invention, there is provided a simple, rapid test for confirming that a given antisense oligomer type provides the required characteristics noted above, namely, high $T_m$, ability to be actively taken up by the host cells, and substantial resistance to RNaseH. This method is based on the discovery that a properly designed antisense compound will form a stable heteroduplex with the complementary portion of the viral RNA target when administered to a mammalian subject, and the heteroduplex subsequently appears in the urine (or other body fluid). Details of this method are also given in co-owned U.S. patent application Ser. No. 09/736,920, entitled "Non-Invasive Method for Detecting Target RNA" (Non-Invasive Method), the disclosure of which is incorporated herein by reference.

Briefly, a test oligomer containing a backbone to be evaluated, having a base sequence targeted against a known RNA, is injected into an animal, e.g., a mammalian subject. The antisense oligomer may be directed against any intracellular RNA, including a host RNA or the RNA of an infecting virus. Several hours (typicaly 8-72) after administration, the urine is assayed for the presence of the antisense-RNA heteroduplex. If heteroduplex is detected, the backbone is suitable for use in the antisense oligomers of the present invention.

The test oligomer may be labeled, e.g. by a fluorescent or a radioactive tag, to facilitate subsequent analyses, if it is appropriate for the mammalian subject. The assay can be in any suitable solid-phase or fluid format. Generally, a solid-phase assay involves first binding the heteroduplex analyte to a solid-phase support, e.g., particles or a polymer or test-strip substrate, and detecting the presence/amount of heteroduplex bound. In a fluid-phase assay, the analyte sample is typically pretreated to remove interfering sample components. If the oligomer is labeled, the presence of the heteroduplex is confirmed by detecting the label tags. For non-labeled compounds, the heteroduplex may be detected by immunoassay if in solid phase format or by mass spectroscopy or other known methods if in solution or suspension format.

B. Exemplary Oligomer Backbones

Examples of nonionic linkages that may be used in oligonucleotide analogs are shown in FIGS. 3A-3G. In these figures, B represents a purine or pyrimidine base-pairing moiety effective to bind, by base-specific hydrogen bonding, to a base in a polynucleotide, preferably selected from adenine, cytosine, guanine and uracil. Suitable backbone structures include carbonate (1A, R=O) and carbamate (3A, R=NH$_2$) linkages (Mertes and Coats 1969; Gait, Jones et al. 1974); alkyl phosphonate and phosphotriester linkages (1B, R=alkyl or —O-alkyl) (Lesnikowski, Jaworska et al. 1990); amide linkages (1C) (Blommers, Pieles et al. 1994); sulfone and sulfonamide linkages (1D, R$_1$, R$_2$=CH$_2$) (Roughten, 1995; McElroy, 1994); and a thioformacetyl linkage (1E) (Matteucci, 1990; Cross, 1997). The latter is reported to have enhanced duplex and triplex stability with respect to phosphorothioate antisense compounds (Cross, 1997). Also reported are the 3'-methylene-N-methylhydroxyamino compounds of structure 1F (Mohan, 1995).

Peptide nucleic acids (PNAs) (FIG. 3G) are analogs of DNA in which the backbone is structurally homomorphous with a deoxyribose backbone, consisting of N-(2-aminoethyl)glycine units to which pyrimidine or purine bases are attached. PNAs containing natural pyrimidine and purine bases hybridize to complementary oligonucleotides obeying Watson-Crick base-pairing rules, and mimic DNA in terms of base pair recognition (Egholm et al., 1993). The backbone of PNAs are formed by peptide bonds rather than phosphodiester bonds, making them well-suited for antisense applications. The backbone is uncharged, resulting in PNA/DNA or PNA/RNA duplexes which exhibit greater than normal thermal stability. PNAs are not recognized by nucleases or proteases.

A preferred oligomer structure employs morpholino-based subunits bearing base-pairing moieties, joined by uncharged linkages, as described above. Especially preferred is a substantially uncharged phosphorodiamidate-linked morpholino oligomer, such as illustrated in FIGS. 1A-1D. Morpholino oligonucleotides, including antisense oligomers, are detailed, for example, in co-owned U.S. Pat. Nos. 5,698,685, 5,217,866, 5,142,047, 5,034,506, 5,166,315, 5,185,444, 5,521,063, and 5,506,337, all of which are expressly incorporated by reference herein.

Important properties of the morpholino-based subunits include: the ability to be linked in a oligomeric form by stable, uncharged backbone linkages; the ability to support a nucleotide base (e.g. adenine, cytosine, guanine or uracil) such that the polymer formed can hybridize with a complementary-base target nucleic acid, including target RNA, with high $T_m$, even with oligomers as short as 10-14 bases; the ability of the oligomer to be actively transported into mammalian cells; and the ability of the oligomer:RNA heteroduplex to resist RNAse degradation.

Exemplary backbone structures for antisense oligonucleotides of the invention include the β-morpholino subunit types shown in FIGS. 2A-2D, each linked by an uncharged, phosphorus-containing subunit linkage. FIG. 2A shows a phosphorus-containing linkage which forms the five atom repeating-unit backbone, where the morpholino rings are linked by a 1-atom phosphoamide linkage. FIG. 2B shows a linkage which produces a 6-atom repeating-unit backbone. In this structure, the atom Y linking the 5' morpholino carbon to the phosphorus group may be sulfur, nitrogen, carbon or, preferably, oxygen. The X moiety pendant from the phosphorus may be fluorine, an alkyl or substituted alkyl, an alkoxy or substituted alkoxy, a thioalkoxy or substituted thioalkoxy, or unsubstituted, monosubstituted, or disubstituted nitrogen, including cyclic structures, such as morpholines or piperidines. Alkyl, alkoxy and thioalkoxy preferably include 1-6 carbon atoms. The Z moieties are sulfur or oxygen, and are preferably oxygen.

The linkages shown in FIGS. 2C and 2D are designed for 7-atom unit-length backbones. In Structure C, the X moiety is as in Structure B, and the moiety Y may be methylene, sulfur, or, preferably, oxygen. In Structure 2D, the X and Y moieties are as in Structure 4B. Particularly preferred morpholino oligonucleotides include those composed of morpholino subunit structures of the form shown in FIG. 2B, where $X=NH_2$ or $N(CH_3)_2$, $Y=O$, and $Z=O$.

As noted above, the substantially uncharged oligomer may advantageously include a limited number of charged linkages, e.g. up to about 1 per every 5 uncharged linkages, more preferably up to about 1 per every 10 uncharged linkages. Therefore a small number of charged linkages, e.g. charged phosphoramidate or phosphorothioate, may also be incorporated into the oligomers.

The antisense compounds can be prepared by stepwise solid-phase synthesis, employing methods detailed in the references cited above. In some cases, it may be desirable to add additional chemical moieties to the antisense compound, e.g. to enhance pharmacokinetics or to facilitate capture or detection of the compound. Such a moiety may be covalently attached, typically to a terminus of the oligomer, according to standard synthetic methods. For example, addition of a polyethyleneglycol moiety or other hydrophilic polymer, e.g., one having 10-100 monomeric subunits, may be useful in enhancing solubility. One or more charged groups, e.g., anionic charged groups such as an organic acid, may enhance cell uptake. A reporter moiety, such as fluorescein or a radiolabeled group, may be attached for purposes of detection. Alternatively, the reporter label attached to the oligomer may be a ligand, such as an antigen or biotin, capable of binding a labeled antibody or streptavidin. In selecting a moiety for attachment or modification of an antisense oligomer, it is generally of course desirable to select chemical compounds of groups that are biocompatible and likely to be tolerated by a subject without undesirable side effects.

C. Preferred Antisense Targets

In practicing the invention, mRNA transcribed from the relevant region of a gene of interest is generally targeted by antisense oligonucleotides; however, single-stranded RNA, double-stranded RNA, single-stranded DNA or double-stranded DNA may be targeted. For example, double-stranded DNA may be targeted using a non-ionic probe designed for sequence-specific binding to major-groove sites in duplex DNA. Exemplary probes are described in U.S. Pat. No. 5,166,315 (Summerton and Weller, 1992), which is hereby incorporated by reference. Such probes are generally referred to herein as antisense oligomers, referring to their ability to block expression of target nucleic acids.

In the methods of the invention, the antisense oligomer is designed to hybridize to a region of the SNAIL nucleic acid sequence, under physiological conditions with a Tm substantially greater than 37° C., e.g., at least 50° C. and preferably 60° C. to 80° C. The oligomer is designed to have high-binding affinity to the nucleic acid and may be 100% complementary to the SNAIL target sequence or may include mismatches, e.g., to accommodate allelic variants, as long as the heteroduplex formed between the oligomer and SNAIL target sequence is sufficiently stable to withstand the action of cellular nucleases and other modes of degradation during its transit from cell to body fluid. Mismatches, if present, are less destabilizing toward the end regions of the hybrid duplex than in the middle. The number of mismatches allowed will depend on the length of the oligomer, the percentage of G:C base pair in the duplex and the position of the mismatch(es) in the duplex, according to well understood principles of duplex stability.

Although such an antisense oligomer is not necessarily 100% complementary to the SNAIL target sequence, it is effective to stably and specifically bind to the target sequence such that expression of SNAIL is modulated. The appropriate length of the oligomer to allow stable, effective binding combined with good specificity is about 8-40 nucleotide base units, and preferably about 12-25 nucleotides. Oligomer bases that allow degenerate base pairing with target bases are also contemplated, assuming base-pair specificity with the target is maintained.

In one preferred approach, the target for modulation of gene expression using the antisense methods of the present invention comprises a sequence spanning or adjacent to the mRNA translational start codon for SNAIL. In an alternative preferred approach, a splice acceptor or donor region of preprocessed SNAIL RNA is targeted. It will be understood that other regions of SNAIL mRNA may be targeted, including one or more of, an initiator or promoter site, an intron or exon junction site, a 3'-untranslated region, and a 5'-untranslated region. It will be further understood that both spliced and unspliced RNA may serve as the template for design of antisense oligomers for use in the methods of the invention (See, e.g., (Hudziak, Summerton et al. 2000).

Exemplary antisense oligomers to SNAIL are provided in Table 1, below. The complement to the SNAIL translational start codon is indicated in bold and the targeted exon/intron boundaries are indicated with the symbol "/" (e.g. SEQ ID NOS: 17-20).

TABLE 1

Exemplary SNAIL Antisense Oligomers

| Name | Antisense Oligomer (5' to 3') Targeting Sequence | Target Ncts. | GenBank Acc. # | SEQ. ID NO. |
|---|---|---|---|---|
| Snail | GGAGCGCGGCATGTTGGCC | 8-26 | M95604 | 11 |
| SNA01 | GTGGTCGAGGCACTGGGGTCG | 49-69 | NM005985 | 12 |
| SNA02 | GCATAGTGGTCGAGGCACTGG | 54-74 | NM005985 | 13 |
| SNA03 | GCGCGGCATAGTGGTCGAGG | 60-79 | NM005985 | 14 |
| SNA04 | GAGCGCGGCATAGTGGTCG | 63-81 | NM005985 | 15 |
| SNA05 | CCTGACGAGGAAAGAGCGCGG | 74-94 | NM005985 | 16 |
| EX1SD | CGCAC/CTGGATTAGAGTCCTG | 203-223 | AF155233 | 17 |
| EX2SA | GAAGGTAAACT/CTGAGGGAG | 892-911 | AF155233 | 18 |
| EX2SD | CACGTAC/CAGTGTGGGTCCG | 1416-1435 | AF155233 | 19 |
| EX3SA | GGCTTCTCGC/CTGGGGAGAG | 4939-4958 | AF155233 | 20 |

In exemplary embodiments of the invention, the antisense oligomer is a PMO containing the sequences presented as SEQ ID NOS:12-20.

The present invention demonstrates that the transcriptional repressor SNAIL is overexpressed in a majority of human colon cancers and that reduction of SNAIL expression by antisense oligomers suppresses colon carcinogenesis. The clinical importance of this observation is supported by the observations in other carcinogenesis systems that SNAIL fosters metastatic spread of tumors and therefore is a molecular target for novel therapeutic agents.

III. Treatment of Peritoneal Dialysis Patients Using Methods of the Invention

In addition to the role of SNAIL in tumor progression and carcinogenesis, it also may play a key role in causing an epithelial to mesenchymal transition (EMT, also referred to as transdifferentiation) in mesothelial cells when they are subjected to peritoneal dialysis. The peritoneal membrane is lined with a layer of epithelial-like mesothelial cells that function as a permeability barrier and secrete various substances that act in the regulation of peritoneal permeability and local host defense. Long-term exposure to the hyperosmotic, hyperglycemic, and acidic solutions used in peritoneal dialysis causes the peritoneum to lose mesothelial cells and undergo fibrosis. These structural alterations are considered to be the leading cause of failure of ultrafiltration and affects approximately 20% of patients undergoing continuous ambulatory peritoneal dialysis (CAPD) (Yanez-Mo, Lara-Pezzi et al. 2003).

The observation that mesothelial cells undergo SNAIL-mediated epithelial-to-mesenchymal transition during CAPD provides another use for the antisense PMO compounds described by this invention. Antisense PMO targeted at the SNAIL gene, as described in detail below for cancer indications, could therefore also be used to prevent the transdifferentiation of peritoneal mesothelial cells and failure of ultrafiltration in patients undergoing peritoneal dialysis. SNAIL antisense PMO added to the dialysis solution would block the expression of SNAIL in the peritoneal mesothelial cells and serve as an effective therapeutic to extend the duration of CAPD available to the dialysis patient.

IV. SNAIL and Alopecia

The studies described in Example 3 have demonstrated that antisense PMO inhibition of SNAIL gene expression can induce alopecia (i.e. hair loss) in mice. As described above, SNAIL binds the E-box motifs of E-cadherin, and therefore inhibits E-cadherin expression. E cadherin is required for proper hair follicle cycling (Young, Boussadia et al. 2003). E-cadherin binds with β-catenin altering its location within the cell as well as reducing its availability. Decreasing the level of SNAIL leads to increased E-cadherin which then limits the availability of β-catenin. The decrease in β-catenin leads to an increase in genes in the NF-kappa beta pathway, including Fas and TRAF1. Studies have shown that Fas knockout mice have decreased chemotherapy induced alopecia (Sharov, Li et al. 2003) indicating that higher levels of Fas could enhance hair loss. Antisense SNAIL PMO administered systemically (e.g. intravenous injection as in Example 3) could cause alopecia through Fas-mediated apoptosis of hair follicle cells or because E cadherin levels have increased sufficiently to cause abnormal hair follicle cycling.

Topical administration of antisense SNAIL PMO is predicted to be a superior method of inducing alopecia. The present invention therefore also provides for a method and composition that induces alopecia and useful in cosmetic applications where hair removal is desired.

V. Treatment of Cancer Using the Methods of the Invention

The invention provides methods for treatment of cancer with an antisense oligonucleotide directed against a nucleic acid sequence encoding SNAIL.

The invention is based on the discovery that a stable, substantially uncharged antisense oligonucleotide, characterized by high Tm, capable of active or facilitated transport into cells, and capable of binding with high affinity to a complementary or near-complementary SNAIL nucleic acid sequence, can be administered to a cancer patient, inhibit expression of SNAIL by a cell resulting in modulation of tumor growth.

A. Treatment of Cancer

In vivo administration of a SNAIL antisense oligomer to a subject using the methods described herein can result in an improved therapeutic outcome for the patient, dependent upon a number of factors including the duration, dose and frequency of SNAIL antisense oligomer administration and the general condition of the subject.

In general, an improved therapeutic outcome relative to a cancer patient refers to a slowing or diminution of the growth of cancer cells or a solid tumor, or a reduction in the total number of cancer cells or total tumor burden.

In preferred applications of the method, the subject is a human subject. The subject may also be a cancer patient, in particular a patient diagnosed as having a carcinoma including, but not limited to: colon, squamous cell, small-cell lung, large-cell lung, embryonal, thyroid, nasopharyngeal, cervical and adrenocortical carcinomas. Other preferred applications of the method include patients with breast carcinoma and malignant melanoma. The patient may have been treated with chemotherapy or radiation therapy or is currently being treated by these methods.

B. Treatment Regimens

The present invention provides methods for cancer therapy, where an oligomer antisense to SNAIL is administered to a patient.

As will be understood by those of skill in the art, the optimal treatment regimen will vary and it is within the scope of the treatment methods of the invention to evaluate the status of the disease under treatment and the general health of the patient prior to, and following antisense oligomer administration in order to determine if additional antisense oligomer administration are indicated. Such evaluation is typically carried out by use of tests typically used to evaluate traditional cancer chemotherapy, as further described below in the section entitled "Monitoring Treatment".

As detailed above, preferred antisense oligonucleotides for use in these methods are substantially uncharged phosphorodiamidate morpholino oligomers (PMOs), characterized by stability, high Tm, and capable of active or facilitated transport as evidenced by (i) competitive binding with a phosphorothioate antisense oligomer, and/or (ii) the ability to transport a detectable reporter into the cells.

In one preferred aspect of this embodiment, the oligomer is a PMO selected from the group consisting of the sequences presented as SEQ ID NOS:12-20.

C. Delivery of Antisense Oligomers to the Patient

Effective delivery of an antisense oligomer to the target SNAIL nucleic acid sequence is an important aspect of the methods of the invention. In accordance with one aspect of the invention, the modes of administration discussed below exploit one of more of the key features: (i) use of an antisense compound that has a high rate of cell uptake, (ii) the ability of the antisense compound to interfere with SNAIL mRNA processing and mRNA translation, and (iii) delivery of the antisense oligomer by a mode of administration effective to achieve high localized concentration of the compound to cancer cells.

In accordance with the invention, effective delivery of an oligomer antisense to SNAIL may include, but is not limited to, various systemic routes, including oral and parenteral routes, e.g., intravenous (IV), subcutaneous, intraperitoneal (IP), and intramuscular; as well as inhalation and transdermal delivery.

It is appreciated that any methods effective to deliver a SNAIL antisense oligomer to into the bloodstream of a subject are also contemplated.

Transdermal delivery of antisense oligomers may be accomplished by use of a pharmaceutically acceptable carrier adapted for e.g., topical administration. One example of morpholino oligomer delivery is described in PCT patent application WO 97/40854, incorporated herein by reference.

Typically, one or more doses of antisense oligomer are administered, generally at regular intervals for a period of about one to two weeks. Preferred doses for oral administration are from about 1 mg oligomer/patient to about 100 mg oligomer/patient (based on an adult weight of 70 kg). In some cases, doses of greater than 100 mg oligomer/patient may be necessary. For IV administration, the preferred doses are from about 0.5 mg oligomer/patient to about 10 mg oligomer/patient (based on an adult weight of 70 kg). The antisense compound is generally administered in an amount sufficient to result in a peak blood concentration of at least 200-400 nM antisense oligomer. Greater or lesser amounts of oligonucleotide may be administered as required and maintenance doses may be lower.

In general, the method comprises administering to a subject, in a suitable pharmaceutical carrier, an amount of the antisense agent effective to inhibit expression of the SNAIL nucleic acid target sequence.

It follows that the antisense oligonucleotide composition may be administered in any convenient vehicle, which is physiologically acceptable. Such an oligonucleotide composition may include any of a variety of standard physiologically acceptable carriers employed by those of ordinary skill in the art. Examples of such pharmaceutical carriers include, but are not limited to, saline, phosphate buffered saline (PBS), water, aqueous ethanol, emulsions such as oil/water emulsions, triglyceride emulsions, wetting agents, tablets and capsules. It will be understood that the choice of suitable physiologically acceptable carrier will vary dependent upon the chosen mode of administration. In some instances liposomes may be employed to facilitate uptake of the antisense oligonucleotide into cells. (See, e.g. (Lappalainen, Urtti et al. 1994; Williams, Camilleri et al. 1996; Lou, Garrett et al. 2001)). Hydrogels may also be used as vehicles for antisense oligomer administration, for example, as described in WO 93/01286. Alternatively, the oligonucleotides may be administered in microspheres or microparticles. Sustained release compositions are also contemplated within the scope of this application. These may include semipermeable polymeric matrices in the form of shaped articles such as films or microcapsules.

It will be understood that the effective in vivo dose of a SNAIL antisense oligonucleotide for use in the methods of the invention will vary according to the frequency and route of administration as well as the condition of the subject under treatment. Accordingly, such in vivo therapy will generally require monitoring by tests appropriate to the condition being treated and a corresponding adjustment in the dose or treatment regimen in order to achieve an optimal therapeutic outcome.

In one preferred embodiment, the oligomer is a phosphorodiamidate morpholino oligomer (PMO), contained in a pharmaceutically acceptable carrier, and delivered orally. In a further aspect of this embodiment, a morpholino SNAIL antisense oligonucleotide is administered at regular intervals for a short time period, e.g., daily for two weeks or less. However, in some cases the antisense oligomer is administered intermittently over a longer period of time.

In some cases, the treatment regimen will include further intervention such as radiation therapy, immunotherapy and/or additional chemotherapy. Such treatment may occur prior to, during or subsequent to administration of the chemotherapeutic agent and SNAIL antisense oligomer.

VI. Evaluating the Effect of Antisense Oligomers

A. Analysis of the Effects of Antisense Oligomer Treatment

Candidate antisense oligomers are evaluated, according to well known methods, for acute and chronic cellular toxicity, such as the effect on protein and DNA synthesis as measured via incorporation of $^3$H-leucine and $^3$H-thymidine, respectively. In addition, various control oligonucleotides, e.g., control oligonucleotides such as sense, nonsense or scrambled antisense sequences, or sequences containing mismatched bases, in order to confirm the specificity of binding of candidate antisense oligomers. The outcome of such tests are important to discern specific effects of antisense inhibition of gene expression from indiscriminate suppression (Bennett and Schwartz 1995). Accordingly, sequences may be modified as needed to limit non-specific binding of antisense oligomers to non-target sequences.

The effectiveness of a given antisense oligomer molecule in forming a heteroduplex with the target RNA may be determined by screening methods known in the art. For example, the oligomer is incubated a cell culture expressing SNAIL, and the effect on the target RNA is evaluated by monitoring the presence or absence of (1) heteroduplex formation with the target sequence and non-target sequences using procedures known to those of skill in the art, (2) the amount of SNAIL mRNA, as determined by standard techniques such as RT-PCR or Northern blot, or (3) the amount of SNAIL protein, as determined by standard techniques such as ELISA or immunoblot (e.g. Western blot).

B. Animal Models

An animal model routinely employed by those of skill in the art to evaluate anti-cancer therapies can be used to demonstrate the efficacy of the methods of the present invention. The Apc$^{Min/+}$ (MIN) mouse is a model for colorectal cancer and was used by the inventors to study the effects of antisense SNAIL PMO on the incidence and development of intestinal precancerous lesions (see e.g. Examples 2&3). The MIN mouse has a germ-line mutation in the adenomatous polyposis coli (Apc) gene which leads to familial adenomatous polyposis (FAP). Inactivation of Apc is found in 80% of sporadic human colorectal cancers and in humans with FAP (Kinzler and Vogelstein 1996). The MIN mouse model mimics the rapid development of adenomatous polyps that affect humans with germ-line inactivation of one Apc gene and therefore is a respected model for human colon carcinogenesis.

Treatment of MIN mice with antisense SNAIL PMO (SEQ ID NO:11) for a period of 4 weeks resulted in a substantial reduction in formation of adenomatous polyps in both the proximal bowel and colon (41.6% and 44.1% reduction, respectively). The total number of tumors was reduced by 21.9% in the PMO treated mice. This observation clearly supports the role of SNAIL in the progression of colon carcinogenesis and as a potent target for anti-carcinogenic therapies.

VII. Monitoring Treatment

The efficacy of a given therapeutic regimen involving the methods described herein, may be monitored, e.g., using diagnostic techniques appropriate to the type of cancer under treatment.

The exact nature of an evaluation will vary dependent upon the condition being treated and the treatment regimen may be adjusted (dose, frequency, route, etc.), as indicated, based on the results of such diagnostic tests.

It will be understood that an effective in vivo treatment regimen using the antisense oligonucleotides of the invention will vary according to the frequency and route of administration, as well as the condition of the subject under treatment (i.e., prophylactic administration versus administration in response to localized or systemic infection). Accordingly, such in vivo therapy will generally require monitoring by tests appropriate to the particular type of condition, e.g., cancer, under treatment and a corresponding adjustment in the dose or treatment regimen in order to achieve an optimal therapeutic outcome.

Diagnosis and monitoring of cancer generally involves one or more of (1) biopsy, (2) ultrasound, (3) x-ray, (4) magnetic resonance imaging, (5) nucleic acid detection methods, (6) serological detection methods, i.e., conventional immunoassay and (7) other biochemical methods. Such methods may be qualitative or quantitative.

The efficacy of a given therapeutic regimen involving the methods described herein may be monitored, e.g., by general indicators of the disease condition under treatment, as further described above.

Nucleic acid probes may be designed based on SNAIL or other nucleic acid sequences associated with the particular cancer under treatment. Nucleic amplification tests (e.g., PCR) may also be used in such detection methods.

It will be understood that the exact nature of diagnostic tests as well as other physiological factors indicative of a disease condition will vary dependent upon the particular condition being treated and whether the treatment is prophylactic or therapeutic.

In cases where the subject has been diagnosed as having a particular type of cancer, the status of the cancer is also monitored using diagnostic techniques typically used by those of skill in the art to monitor the particular type of cancer under treatment.

The antisense oligomer treatment regimen may be adjusted (dose, frequency, route, etc.), as indicated, based on the results of immunoassays, other biochemical tests and physiological examination of the subject under treatment.

Material and Methods

Archived colon cancer samples from Evanston-Northwestern Healthcare were utilized for optimizing antibody conditions and assessing SNAIL expression in the uninvolved mucosa. For quantitation of the proportion of tumors that were SNAIL positive, we employed a tissue array (Imgenex, San Diego Calif.) in order to provide uniformity in staining parameters. This array contained 59 human colon cancers and provided information on their pathological stage (33 cancers stage II, 23 cancers stage III and 6 cancers stage IV), age (mean age 56.9 years) gender (38 cancers in males and 21 in females) and location (29 cancers proximal to splenic flexure and 30 in the distal colon). Immunohistochemical staining was performed as described (Roy, Olusola et al. 2002). Briefly, slides were heated to 60° C. for one hour, deparaffinized using xylene and hydrated by a graded series of ethanol washes. Antigen retrieval was accomplished by microwave heating in antigen unmasking solution (Vector Labs, Burlingame Calif.). Endogenous peroxidase activity was quenched by a 5 minute incubation in 3% $H_2O_2$ and nonspecific binding was blocked with serum. Sections were then probed with one of two affinity purified antibodies raised against distinct internal epitopes of human SNAIL (T-18 and E-18, Santa Cruz Biotechnology, Santa Cruz Calif.) at a dilution of 1:100 overnight at 4° C. Slides were developed with the Vectastain Elite Kit (Vector Labs, Burlingame Calif.) and were scored by a gastrointestinal pathologist on a 4 point scale. Any specific tumor staining was considered positive. Statistical analysis was performed by chi-squared test.

Ten week-old MIN mice were injected intraperitonealy (IP) with SNAIL PMO (SEQ ID NO: 11) at a dose of 250 μg per day, five days per week for four weeks. Control mice were not injected with any antisense compound and were allowed to develop colon cancers.

EXAMPLE 1

SNAIL is Overexpressed in Human Colon Cancer

SNAIL immunoreactivity was not detected in the uninvolved mucosa despite marked staining in the tumor sections on the same slide. Dramatic SNAIL expression was noted in most but not all colon cancer samples. The specificity of the staining is supported by negligible background staining in the stromal elements and also through the employment of negative controls (incubation with non-immune sera alone). Moreover, in the tissue array, there were negative tumors juxtaposed against markedly positive tumors. We corroborated our findings by probing a subset of colon cancer slides with a second primary antibody (raised to a different internal epitope of human SNAIL) and this yielded comparable results.

Scoring of slides by a gastrointestinal pathologist indicated that SNAIL was present in 78% of tumors (46/59). The utilization of a tissue array provided reliable quantitation by mitigating the batch-to-batch variability common in immunohistochemistical studies. Of the tumors that were SNAIL positive, 67% had mild (1+) intensity of staining whereas moderate (2+) and marked (3+) immunoreactivity was noted in 24% and 9%, respectively.

Subgroup analysis failed to detect any significant differences in the proportion of positive tumors with regards to demographic characteristics such as tumor location (21/29 distal tumors versus 25/30 proximal tumors, p=0.31) and gender (28/38 in males versus 18/21 in females, p=0.29). There was, however, a significantly higher average age from colon cancer cases which were positive for SNAIL (58.9±12.7 years) compared with those that were negative (49.8±12.7) which was statistically significant (p=0.028 by t-test). There was no discernable correlation between any of these demographic factors and the staining intensity for SNAIL. In order to assess whether SNAIL may foster metastatic spread, we compared advanced tumors (in order to control for depth of invasion etc) and noted a trend towards increased presence of SNAIL in tumors that had spawned distant metastasis (15/23 for stage III versus 6/6 tumors for stage IV). However, because of the small numbers of advanced tumors in these subgroups, this difference failed to achieve statistical significance (p=0.11)

EXAMPLE 2

The Transcriptional Repressor SNAIL Regulates E-Cadherin in Colon Carcinogenesis and During Chemoprevention Loss of the tumor suppressor gene E-cadherin is important for initiation and progression of colorectal carcinogenesis. Moreover, we and others have reported tha E-cadherin induction is a common theme in chemoprevention of colorectal cancer (CRC). However, the mechanism for epigenetic silencing of E-cadherin and its reseversal by NSAIDS remain unclear. In several tumor types (E.g. beast, melanoma, hepatomas), upregulation of the transcriptional repressor SNAIL has been implicated in the epigenetic E-cadherin loss. Therefore, the role of SNAIL in colon carcinogenesis was investigated.

For chemopreventive studies, we treated the human CRC cell line HCT-116 with sulindac sulfide (100 μM) or vehicle for 3 days and analyzed SNAIL and E-Cadherin by RT-PCR. In order to evaluate frequency of SNAIL overexpression in human colon cancer, we immunohistochemically probed a tissue array using a poly clonal antibody. Finally, to determine whether SNAIL is implicated in E-cadherin donwregulation in CRC, we treated 10 week old male MIN mice with antisense PMO to SNAIL (250 μg/day for 5 weeks) and examined E-cadherin levels in the uninvolved intestine using Western blot analysis.

In HCT-116 cells, treatment with 100 μM sulindac sulfide induced apoptosis and inhibited proliferation. SNAIL expression was dramatically suppressed (to 39.2% of vehicle, p=0.007) with a concomitant induction in E-cadherin. SNAIL immunoreactivity was detected in 76% (46 out of 59) of CRCs. SNAIL positive tumors tended to occur in older patients (age 58+12.7 versus 49.8+12.7, p=0.028) and manifested a trend towards increased metastatic disease (p=0.11). Finally, anti-SNAIL PMO resulted in a 26% increase in intestinal E-cadherin protein in the MIN mice (p=0.027), suggesting that SNAIL is responsible, at least partly, for E-cadherin downregulation in colon carcinogenesis.

These observations demonstrate that SNAIL is overexpressed in most colorectal cancer. The data implicates SNAIL overexpression as a mechanism through which E-cadherin is lost during colon carcinogenesis. Furthermore, SNAIL may represent an important molecular target for NSAIDS in the chemoprevention of CRC resulting in the induction of E-cadherin.

EXAMPLE 3

Selective Downregulation of Transcriptional Suppressor SNAIL Decreases Intestinal Tumorigenesis in APC$^{MIN}$ Mouse Upregulation of the transcriptional repressor, SNAIL has been shown to impart a more aggressive phenotype in a variety of human cancers including breast. While little is known on SNAIL regulation in colorectal cancer (CRC), we have observed that SNAIL is overexpressed in 80% of CRC and is downregulated by chemopreventive agents such as NSAIDS and Polyethylene glycol. In order to investigate the importance of SNAIL in CRC development and prevention, we investigated the phenotype of the APC$^{MIN}$ mouse model in which SNAIL was selectively downregulated. The APC$^{MIN}$ mouse (MIN) is a useful model system to study colon carcinogenesis as they are genetically determined to develop colon cancer (Moser, Pitot et al. 1990; Corpet and Pierre 2003).

Sixteen MIN mice (9-10 week old) were randomized to daily i.p. injections for 5 weeks with either saline or anti-SNAIL phosphorodiamidate morpholino antisense oligomers (PMO; 200 μg/20 g mouse). Animals were given BrdU 2 h prior to sacrifice and intestinal tumors were scored under magnification by observers blinded to treatment group. Immunohistochemical analysis was performed on formalin fixed intestinal segments for proliferation (BrdU labeling), apoptosis (using activated caspase 3) and SNAIL downregulation. The samples were scored by a gastrointestinal pathologist.

As shown in Table 2 below, SNAIL antisense PMO caused a significant decrease in immunohistochemical expression of SNAIL. Antisense treatment also significantly decreased the development of tumors in the MIN mouse. The antisense treated MIN mice exhibited reduced rate of mucosal proliferation and increased apoptosis.

TABLE 2

|  | Control APC$^{MIN}$ | APC$^{MIN}$/ SNAIL PMO |
|---|---|---|
| Tumor incidence (%) | 25.06 ± 4.10 | 19.57 ± 6.16 |
| SNAIL (Arbit. Units) | 2.58 ± 0.67 | 2.00 ± 0.58 |
| Cleaved Caspase-3 (Arbit. Units) | 1.00 ± 0.74 | 1.50 ± 0.65 |
| BrdU Positive (% Total) | 8.92 ± 8.00 | 3.43 ± 3.80 |

$p < 0.05$;
Control MIN mice as compared to MIN mice treated with SNAIL antisense Antisense PMO to SNAIL was able to significantly suppress MIN mouse tumorigenesis through induction of apoptosis and possibly inhibition of proliferation. While the antitumorigenic effects with this regimen of antisense PMO treatment were moderate (22% decrease), probably reflected by a modest suppression of SNAIL protein expression (23%), this data provides the first evidence implicating SNAIL in experimental colon carcinogenesis. These studies demonstrate that targeting SNAIL may be an important anti-CRC strategy.

In addition to the observed antitumorigenic effect of decreased SNAIL expression in the antisense treated MIN mice, the PMO treated animals demonstrated pronounced hair loss (alopecia).

Sequence listing

| Target Sequences (5' to 3') | SEQ ID NO. | GenBank Acc. No. | Location |
|---|---|---|---|
| GGCCAACATGCCGCGCTCC | 1 | M95604 | 8-26 |
| CGACCCCAGTGCCTCGACCAC | 2 | NM005985 | 49-69 |
| CCAGTGCCTCGACCACTATGC | 3 | NM005985 | 54-74 |
| CCTCGACCACTATGCCGCGC | 4 | NM005985 | 60-79 |
| CGACCACTATGCCGCGCTC | 5 | NM005985 | 63-81 |
| CCGCGCTCTTTCCTCGTCAGG | 6 | NM005985 | 74-94 |
| CAGGACTCTAATCCAGGTGCG | 7 | AF155233 | 203-223 |
| CTCCCTCAGAGTTTACCTTC | 8 | AF155233 | 892-911 |
| CGGACCCACACTGGTACGTG | 9 | AF155233 | 1416-1435 |
| CTCTCCCCAGGCGAGAAGCC | 10 | AF155233 | 4939-4958 |

Sequence listing

| Oligomer Targeting Sequences (5' to 3') | SEQ ID NO. | GenBank Acc. No. | Location |
|---|---|---|---|
| GGAGCGCGGCATGTTGGCC | 11 | M95604 | 8-26 |
| GTGGTCGAGGCACTGGGGTCG | 12 | NM005985 | 49-69 |
| GCATAGTGGTCGAGGCACTGG | 13 | NM005985 | 54-74 |
| GCGCGGCATAGTGGTCGAGG | 14 | NM005985 | 60-79 |
| GAGCGCGGCATAGTGGTCG | 15 | NM005985 | 63-81 |
| CCTGACGAGGAAAGAGCGCGG | 16 | NM005985 | 74-94 |
| CGCACCTGGATTAGAGTCCTG | 17 | AF155233 | 203-223 |
| GAAGGTAAACTCTGAGGGAG | 18 | AF155233 | 892-911 |
| CACGTACCAGTGTGGGTCCG | 19 | AF155233 | 1416-1435 |
| GGCTTCTCGCCTGGGGAGAG | 20 | AF155233 | 4939-4958 |

SEQ ID NO:21

*Homo sapiens* snail zinc finger protein (SNAI1) gene, complete cds. GenBank ACCESSION No. AF115233

```
   1 cccaccccc accacccccc ggagtactta agggagttgg cggcgctgct gcattcattg
  61 cgccgcggca cggcctagcg agtggttctt ctgcgctact gctgcgcgaa tcggcgaccc
 121 cagtgcctcg accactatgc cgcgctcttt cctcgtcagg aagccctccg accccaatcg
 181 gaagcctaac tacagcgagc tgcaggactc taatccaggt gcgttggagg ggttctgggc
 241 tccaggaggt ttgggggaga caggcgaagg ctgcgtgggg ggcacctgag ggaggcggcc
 301 tgcctgagcc aggatcgagt cacaggatgt tttgtggacc attgcgggct cgggagaccg
 361 ggcaagtggg tccccagttc cggggatctg tctgggtggt tgggggagtg ccgtgtagag
 421 ggcaggggtc ttcagcttgg ggggcctttg tagccggcga gaggcggagg agctccgcaa
 481 gaggggaagg agaggaggcc tgtgtcagga gggccctctg gacgctgctg gggagagtcc
 541 ggagtccaga gggttgaggg gagggtggg gagacgagat gtgtgtgagg aggggattg
 601 gggcagggtg gtggctccgg ggctgggatg atgggttct ggcctcaggc tggagactgg
 661 ggacttagga gagggagatc aggaaatgac ctccttcaac tgggggtcct acgtgtgaga
 721 gactcagatt gggtgacctg ggcgaggagg gcaggaacct ggtctgtcct gtggataatt
 781 ttttttgatct aattatgtat tgagaatcgg ccccacccag cccctggcca gcggtgggct
 841 catgtttgtt gattgagtga atgatttaat taacgcctga ctctgctttt tctccctcag
 901 agtttacctt ccagcagccc tacgaccagg cccacctgct ggcagccatc ccacctccgg
 961 agatcctcaa ccccaccgcc tcgctgccaa tgctcatctg ggactctgtc ctggcgcccc
1021 aagcccagcc aattgcctgg gcctcccttc ggctccagga gagtcccagg gtggcagagc
1081 tgacctccct gtcagatgag gacagtggga aaggctccca gccccccagc ccaccctcac
```

-continued

```
1141 cggctccttc gtccttctcc tctacttcag tctcttcctt ggaggccgag gcctatgctg
1201 ccttcccagg cttgggccaa gtgcccaagc agctggccca gctctctgag gccaaggatc
1261 tccaggctcg aaaggccttc aactgcaaat actgcaacaa ggaataccto agcctgggtg
1321 ccctcaagat gcacatccga agccacacgc tgccctgcgt ctgcggaacc tgcgggaagg
1381 ccttctctag gccctggctg ctacaaggcc atgtccggac ccacactggt acgtgcccct
1441 ccaggcgccc ccaccgttgc tctctctggc agcttttgtg aatctgggct tgctgttctc
1501 attcccaaag ctgtggacac tgaggccccg agtcttctaa cttctagctc aagttccagg
1561 gcctggctct ctggaaacgt ttggcagaaa ctttcttcat cagctaagca gatgggcaaa
1621 gcagacacct tcccaatccc ctgcagcctg tttctcagcc aaatgggtcg agctggata
1681 tgggaaaggt gcaaccaaca ccttgctgtg ggggccaggt gtgaaggggc ccacccggcc
1741 acaccctctc ccgggtccgc cccctcccta gccagacagg atgttgtcag accccccgcc
1801 tggctctgaa tccttctttg agaactttct caaaacttag gctgatgttt ctcttctgtg
1861 agcctcattt tctctatctt tcagatgggc atgagaacag cttttggggt ttctatacag
1921 gctaaatgca ggaatgcata tgggaagcac ctggcaaagt gccggtacct gctaaactct
1981 cacaaaaatg gttccttggc atttgctctg cttccttgct gtgtgacttt gggcaagcaa
2041 cttaacctct ctgagcctta ggggaaaact atgatagcat atgttttaga gagtggctgt
2101 aaaggtggct aatcactta tagtaattta ttatacccga acggttctca ggtcggcttc
2161 cccaccccca ctgaatccta gcacacagac caggaaacgg catctttggg gcagaaaaca
2221 caatcacgtc ttttgaaaat ttactaaatg tgtaaaaaac tttctggaca tggagaaaag
2281 gtagaacttt ttagaacttg aatggtqgca gccactgtgc ctggagctgc tctttggaga
2341 gtgacagttg agggagaaga ttccacaggg ttcaagctgg ccaggttctg ccatttcctg
2401 gcctggcgcc tgacctctga gcggtgaggg ttagtgaggt gtctgggagg actggcaatt
2461 cgcgggcttt attggcatct tattcgacta aggctaccca tttctcttcc ttcgtgcacc
2521 aattgctctg attttaacat gtaaaggtcc aactgcctgg cctcctgggt gcctgcccag
2581 ctcacagggc tctattttgg gacagttgaa ccctcaggg tgctgcagtc ctgcctgcct
2641 ctctcacctc ccatctggac attattttaa tgtaaaggca tggctgagac acagaaatcc
2701 ccttgaaatg tatcattgcg gtcctcattg actcccattg tgtgccttaa tggtgggccc
2761 agtgggtggg ggctgggagg ggtggagcag gtgcatgggg cagcggtgcc cagcacctgt
2821 tccagtcaca gctgctggcc cactgcatgg caggcccctt taatccgggg atatcgcatg
2881 tacagtgccc cctcggcgc ccttttgtccc cgccggcctg gtgccgattt cacacttgcc
2941 aggagtacca tgaaggcgtc tggggggcga gggatccaag gagtgggggt ctgtgcctcc
3001 tgcgtgtgca cacagccccc gccccagcc catcatgtcc tagaatgtct ccttcccctt
3061 ttgtttgggt tcaggtctca tcacactttg ggcacttact gtacaggagg gtagtgctca
3121 ggacttcacc aacagccctg ggaagggaag ggaggtgctg tcctaactct ggtcttacaa
3181 atggactcca gccccttttc cagatctcca gagtcagccc ttagttcaca agggtgaact
3241 taccttctc attcacatga agacttagaa tgcaatcaac aaaccctca ggcgtggcgt
3301 gtggaggctg ctgagtaatg gcagagtgga gtagtgctca ggcaccctc ccccaatcct
3361 ctatgtcccc cacccttgg agtggcgagt ttccattct gccccatgag actgagtcca
3421 gctctcaggc gctccataag tcctattga atgcatgggt cccattggag ccatcctctg
3481 gactctctcc taccctggta gctcagtgtg gcaccctagg cacccaggag gtgatggaat
```

-continued

```
3541 gaattcactc tcagctctta aattccatcc agcgctggga tttcacaggc gggccctgac
3601 cttgcgggca tatcagactg ggcgtgaggg gattggagaa ttgcatgttt tttaaaaga
3661 ctattcagta ttatggaata gtgtctagca cttagtagga gctcagtaga ttaaaaaaaa
3721 aattatagac agggtcttgc tttatcgcct aggcttgtct caaactcctg gcttcaagca
3781 atcctgcctc actcggcctc ccagagtgat gggattacaa gcgtgagcca ccacacccag
3841 cctcaataga ttttttgttta atgggttact gttatgacct tttatttgga aaatgctgca
3901 tcccccagaa aaaaacaaat caacattatt ggtgtttttg gaactatata gcttttggt
3961 tggagcaggg attgttatga ggcatgagtg aggggcaga ctcctctgag gcctctttaa
4021 tttttaaaac agacttattt attctctaag ggcttgttga ggatttactg ggcacccagc
4081 tccatgtgca agacttttcc caacacagcc ttggccaggc agatggtgtg tcagggccac
4141 aggtttccgt agcctcttgg gtgatagaaa ggggcccagg ccctgggctg ggctcagaa
4201 gggactcaaa ggaggccctt gcccttatgg gactcagcct gattggagaa cagacaagga
4261 gatttgggat tacagcgcag gaggtggggt ggtgaggaaa gcaggctgct ggccgggccc
4321 caggagtggc ctaaccagct tggaggtggg ggtgggaag cctcttaagg ctgactctgg
4381 ctttggcccc caacagagta aatcaaggaa tgactccagg actgatggta aggacaccag
4441 tcacgtcctc ccttgactga aggcagtaag ggcagtaggt gaaatcagag gctttggggt
4501 cctgccaggg gaacctgaac atgctacttc tgggcctcag tttcactgtc tctgaaatga
4561 gaccacagta ggatcaagtg acagtaggat gaatcagtaa aggtgttgag tcattgttga
4621 ccacttcgca cgtccctgcg ggatgtggat gagtacccta ccttctgtca cttatcaacc
4681 cctatgagtg gggggtgaat agccccattt tacaggtggg aaaatggagg ctcagagaag
4741 ccagacaact tgctcagagt tgcacagtgg gaagcagcag agctccgtca ggtcccggcc
4801 tttggaccct ggctgtgtgt ttgacggagg cctggctttc ctgggatcat gggattcttt
4861 cagggtttgg ggtatgcggg gagggattcc catcactgcc agccgttgtc ccacggctca
4921 ctcggccttt ctggcgttct ctccccaggc gagaagccct tctcctgtcc ccactgcagc
4981 cgtgccttcg ctgaccgctc caacctgcgg gcccacctcc agacccactc agatgtcaag
5041 aagtaccagt gccaggcgtg tgctcggacc ttctcccgaa tgtccctgct ccacaagcac
5101 caagagtccg gctgctcagg atgtccccgc tgaccctcga ggctccctct tcctctccat
5161 acctgcccct gcctgacagc cttcccagc tccagcagga aggacccac atccttctca
5221 ctgccatgga attccctcct gagtgcccca cttctggcca catcagcccc acaggacttt
5281 gatgaagacc attttctggt tctgtgtcct ctgcctgggc tctggaagag gccttcccgt
5341 ggccatttct gtggagggag ggcagctggc ccccagccct gggggattcc tgagctggcc
5401 tgtctgcgtg ggttttttgta tccagagctg tttggataca gctgctttga gctacaggac
5461 aaaggctgac agactcactg ggaagctccc accccactca ggggacccca ctcccctcac
5521 acaccccccc ccacaaggaa ccctcaggcc accctccacg aggtgtgact aactatgcaa
5581 taatccaccc ccaggtgcag ccccaggcc tgcggaggcg gtggcagact agagtctgag
5641 atgccccgag cccaggcagc tatttcagcc tcctgtttgg tggggtggca cctgtttccc
5701 gggcaattta acaatgtctg aaagggact gtgagtaatg gctgtcactt gtcggggcc
5761 caagtgggt gctctggtct gaccgatgtg tctcccagaa ctattctggg ggcccgacag
5821 gtgggcctgg gaggaagatg tttacatttt taaaggtaca ctggtattta tatttcaaac
5881 attttgtatc aaggaaacgt tttgtatagt tatatgtaca gtttattgat attcaataaa
```

```
5941 gcagttaatt tatatattaa aaagtctttg gtgtcataga ggagtgggta ttttgaaagg
6001 tctttggtaa gggaggaggg gacaggaatt cctgaagctt agatatttct gacacagcct
6061 taaatcttgt ccttggaaac atcataggc tttggagtcc tgggtgtcac tgtcagggac
6121 cttatgagac tgggttttcc cgttggcctg gtgtcctgt ctgctgctgt ttgggtgagc
6181 cagcggcatc catacgagct cttcactata cactgtggct ttttactttc tcgttcttga
6241 attttgaagt tgatctgg
```

| Transport Peptide Sequences | SEQ ID NO. | Name |
|---|---|---|
| NH$_2$-RRRRRRRRRFFC-CO$_2$H | 22 | R$_9$F$_2$C |
| NH$_2$-RRRRRFFRRRRC-CO$_2$H | 23 | R$_5$F$_2$R$_4$C |
| NH$_2$-RAhxRRAhxRRAhxRRAhxR-CO$_2$H | 24 | (RAhxR)$_4$ |

The invention claimed is:

1. A method of treating colorectal cancer in a subject, comprising:
administering to a subject a therapeutically effective amount of a composition of a morpholino antisense oligonucleotide, wherein the oligonucleotide is of about 10-40 bases in length, comprises a nuclease-resistant backbone and a targeting sequence which forms a heteroduplex with a target region of processed or preprocessed human SNAIL RNA transcript affecting expression of SNAIL protein, and inhibits expression of active SNAIL protein in target cancer cells.

2. The method of claim 1, wherein the preprocessed SNAIL RNA transcript has the sequence of SEQ ID NO:21.

3. The method of claim 1, wherein the heteroduplex has a Tm of dissociation of at least 45° C.

4. The method of any one of claims 1, 2 or 3, wherein the oligonucleotide is composed of morpholino subunits and phosphorus-containing intersubunit linkages joining a morpholino nitrogen of one subunit to a 5' exocyclic carbon of an adjacent subunit.

5. The method of claim 4, wherein the intersubunit linkages are uncharged.

6. The method of claim 4, wherein the morpholino subunits are joined by intersubunit linkages, in accordance with the structure:

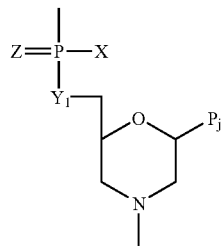

where $Y_1$=O, Z=O, Pj is a purine or pyrimidine base-pairing moiety effective to bind, by base-specific hydrogen bonding, to a base in a polynucleotide, and X is alkyl, alkoxy, thioalkoxy, amino, aklyamino, or dialkylamino.

7. The method of claim 1, wherein the administered composition is a conjugate of the oligonucleotide and an arginine-rich polypeptide effective to promote uptake of the oligonucleotide into target cells.

8. The method of claim 7, wherein the arginine-rich peptide is covalently coupled at its C terminus to the 3' end of the antisense compound.

9. The method of claim 1, wherein the antisense oligonucleotide target region is a translation start site of the processed SNAIL transcript.

10. The method of claim 1, wherein the antisense oligonucleotide target region is a splice site of the preprocessed human SNAIL transcript.

11. The method of claim 1, wherein the antisense oligonucleotide is effective to inhibit cancer cell growth.

12. The method of claim 1, which further includes administering an additional chemotherapeutic agent to the subject.

* * * * *

Adverse Decisions in Interference

Patent No. 7,402,574, Patrick L. Iversen, Hemant K. Roy and Richard K. Bestwick, ANTISENSE COMPOSITION AND METHOD FOR TREATING CANCER, Interference No. 105,732, final judgment adverse to the patentees rendered March 4, 2010, as to claims 1-12.

(*Official Gazette*, *July 27, 2010*)